United States Patent
Gilmer et al.

(10) Patent No.: US 11,224,614 B2
(45) Date of Patent: Jan. 18, 2022

(54) COMPOSITIONS AND METHODS FOR INCREASING IRON INTAKE IN A MAMMAL

(71) Applicant: Solvotrin Therapeutics Limited, Cork (IE)

(72) Inventors: John Gilmer, County Dublin (IE); Gabor Radics, Dunshaughlin (IE); Michael Whelehan, Newtown (IE); Jun Wang, Dun Laoghaire (IE); Pat O'Flynn, Douglas (IE); Mark Ledwidge, Douglas (IE)

(73) Assignee: Solvotrin Therapeutics Limited, Cork (IE)

( * ) Notice: Subject to any disclaimer, the term of this patent is extended or adjusted under 35 U.S.C. 154(b) by 93 days.

(21) Appl. No.: 14/854,373

(22) Filed: Sep. 15, 2015

(65) Prior Publication Data
US 2016/0073668 A1   Mar. 17, 2016

Related U.S. Application Data

(60) Provisional application No. 62/146,897, filed on Apr. 13, 2015.

(30) Foreign Application Priority Data

Sep. 15, 2014   (GB) .................................... 1416293

(51) Int. Cl.
*A61K 33/26* (2006.01)
*A61K 9/16* (2006.01)
*A61K 9/20* (2006.01)

(52) U.S. Cl.
CPC ............ *A61K 33/26* (2013.01); *A61K 9/1658* (2013.01); *A61K 9/1694* (2013.01); *A23V 2002/00* (2013.01); *A61K 9/2063* (2013.01)

(58) Field of Classification Search
None
See application file for complete search history.

(56) References Cited

U.S. PATENT DOCUMENTS 505,986 A   10/1893   Marfori et al.
4,067,994 A   1/1978   Anderson et al.
(Continued)

FOREIGN PATENT DOCUMENTS

CL   2014000066 A1   6/2014
CN   1557481 A   12/2004
(Continued)

OTHER PUBLICATIONS

Martin et al., "Impact of protein pre-treatment conditions on the iron encapsulation efficiency of whey protein cold-set gel particles"—Eur Food Res Technol, 2012, pp. 995-1003.*
(Continued)

*Primary Examiner* — Elizabeth Gwartney
(74) *Attorney, Agent, or Firm* — Foley & Lardner LLP

(57) ABSTRACT

Compositions containing iron and denatured protein have been prepared that are capable of increasing serum iron and other divalent metal cations in a subject. For example, edible microbeads have been prepared containing iron entrapped within a protein matrix that provides a gastroprotective effect and improves iron bioavailability relative to previously known vehicles for delivering iron to a subject.

21 Claims, 22 Drawing Sheets

(56) References Cited

U.S. PATENT DOCUMENTS

| | | | |
|---|---|---|---|
| 4,167,564 A | 9/1979 | Jensen | |
| 4,216,144 A | 8/1980 | Ashmead | |
| 4,493,829 A | 1/1985 | Sportoletti et al. | |
| 4,746,730 A | 5/1988 | De Ambrosi et al. | |
| 5,418,010 A * | 5/1995 | Janda | A61K 9/1658 264/4.1 |
| 8,512,748 B2 | 8/2013 | Pearnchob et al. | |
| 2005/0170062 A1* | 8/2005 | Burling | A23C 9/1307 426/601 |
| 2006/0134227 A1* | 6/2006 | Bortz | A61K 31/19 424/646 |
| 2009/0124572 A1 | 5/2009 | Nelson | |
| 2013/0209577 A1* | 8/2013 | Bortz | A61K 31/198 424/648 |

FOREIGN PATENT DOCUMENTS

| | | |
|---|---|---|
| CN | 101102762 A | 1/2008 |
| CN | 101143011 A | 3/2008 |
| CN | 101928742 A | 12/2010 |
| CN | 102869271 A | 1/2013 |
| CN | 105324033 A | 2/2016 |
| EP | 0 979 614 A2 | 2/2000 |
| EP | 0 979 614 A3 | 5/2000 |
| WO | WO-01/12163 A1 | 2/2001 |
| WO | WO-2007/035757 A2 | 3/2007 |
| WO | WO-2012/097155 A1 | 7/2012 |
| WO | WO-2013/044246 A1 | 3/2013 |
| WO | WO-2016/041988 A1 | 3/2016 |

OTHER PUBLICATIONS

Martin et al., "Enhancing the in vitro Fe2+ bio-accessibility using ascorbate and cold-set whey protein gel particles", Dairy Sci. & Technol., 92, 2012, pp. 133-149.*

Remondetto et al., "Iron Availability from Whey Protein Hydrogels: An in Vitro Study", Journal of Agricultural and Food Chemistry, 52, 2004, pp. 8137-8143.*

Remondetto et al.,"Iron Availability from Whey Protein Hydrogels: An in Vitro Study"—J. Agric. Food Chem., 2004, 52, pp. 8137-8143. (Year: 2004).*

Martin, et al., "Enhancing the in vitro Fe2 bio-accessibility using ascorbate and cold-set whey protein gel particles", Dairy Sci. & Technol., 2012, vol. 92, pp. 133-149.

Martin, et al., "Impact of protein pre-treatment conditions on the iron encapsulation efficiency of whey protein col-set gel particles", Eur Food Res Technol, 2012, vol. 234, pp. 995-1003.

Zhang, et al., "Bioavailability of Iron-Milk-Protein Complexes and Fortified Cheddar Cheese", Dairy Foods Research Papers, 309, Journal of Dairy Science, vol. 72, Nov. 1989, No. 11, pp. 2845-2855.

Final Office Action dated Jul. 24, 2020, from U.S. Appl. No. 16/085,336.

He, et al., "Comparison of iron uptake from reduced iron powder and FeSO4 using the Caco-2 cell model: effects of ascorbic acid, phytic acid, and PH," J Agric Food Chem, Apr. 23, 2008, 56(8), pp. 2637-2642, abstract only.

Kroe, et al., "Interrelation of amino acids and pH n intestinal iron absorption," American Journal of Physiology, Aug. 1, 1966, abstract only, 3 pages.

Non-Final Office Action dated Dec. 12, 2019, from U.S. Appl. No. 16/085,336.

Non-Final Office Action dated Jul. 21, 2021, from U.S. Appl. No. 16/085,336.

Remondetto, et al., "Cold Gelatin, of Beta-lactoglobulin in the Presence of Iron," JFS: Food Chemistry and Toxicology, vol. 67, Nr. 2, 2002, pp. 586-595.

Restriction Office Action dated Aug. 1, 2019, from U.S. Appl. No. 16/085,336.

Teucher, et al., "Enhancers of Iron Absorption: Ascorbic Acid and other Organic Acids," International Journal for Vitamin and Nutrition Research, 2004, 74, pp. 403-419, abstract only, 1 page.

Walker, et al., "Bioavailability of iron in oral ferrous sulfate preparations in healthy volunteers," CMAJ, vol. 141, Sep. 5, 1989, pp. 543-547.

* cited by examiner

COMPOSITIONS AND METHODS FOR INCREASING IRON INTAKE IN A MAMMAL

CROSS-REFERENCE TO RELATED APPLICATIONS

This application claims priority to U.S. provisional application No. 62/146,897, filed Apr. 13, 2015, and GB patent application no. 1416293.7, filed Sep. 15, 2014, the contents of which are incorporated herein by reference.

TECHNICAL FIELD

The invention relates to compositions suitable for delivering iron to a mammal.

BACKGROUND TO THE INVENTION

Oral iron is often poorly absorbed and tolerated in mammals, and according to the World Health Organisation (WHO) iron deficiency affects more than two billion people in developed and developing countries. This can result in adverse effects on cognitive function, oxygen transport, metabolism and immune function.

Iron is predominantly supplemented orally as the ferrous (Fe 2+) iron, which is absorbed actively in response to body need through the divalent metal transporter 1 (DMT-1), yet has poor oral bioavailability and tolerability. Ferric (Fe 3+) iron is usually better tolerated from a gastrointestinal point of view but tends to have poorer bioavailability than ferrous iron. Ferrous sulfate continues to be recommended by the WHO as the preferred form of iron for oral administration. Delayed release and/or gastroprotective formulations (for example enteric coated) with and without iron have been marketed but are long acknowledged to persons known in the art to be less bioavailable and, accordingly, are not recommended. See, e.g., Walker S., et al., "Bioavailability of iron in oral ferrous sulfate preparations in healthy volunteers," Canadian Medical Association Journal 1989; (141): 543-547. Current forms of oral iron used for supplementation have significant limitations, helping to explain the high incidence of iron deficiency, the only nutritional deficiency prevalent in developing and developed countries.

SUMMARY OF THE INVENTION

One embodiment of the invention is a composition comprising iron and a carrier comprising denatured protein, wherein the composition releases less than 70% or less than 50 wt % of the total iron content as ferrous iron over the course of one hour in simulated gastric fluid at pH 1.6, and wherein the composition, when administered orally to a human, has a relative bioavailability of at least 120% that of an equimolar dose of an orally administered solution of ferrous sulfate in acidified water.

In one embodiment, the composition has an iron:protein ratio, by weight, of 1:500 to 1:5.

In one embodiment, the composition is largely amorphous.

In one embodiment, the denatured protein is at least 50%, 80% or 90% denatured.

In one embodiment, the denatured protein contains at least 50%, 80% or 90% denatured beta lactoglobulin.

In one embodiment, the moisture content of the composition is less than 10% by weight.

In one embodiment, the carrier comprises a core and a skin, wherein skin comprises a denatured aggregated protein. Optionally, the skin further comprises a gelling agent.

In one embodiment, the core comprises a denatured aggregated protein matrix. Optionally, the denatured protein contains, excluding iron, less than 1% divalent metal ions (w/v).

In one embodiment, the composition, when administered orally to a human, has a relative bioavailability of at least 130%, 140% or 150% that of an equimolar dose of an orally administered solution of ferrous sulfate in acidified water.

In one embodiment, the composition releases less than 50 wt % of the total iron content as ferrous iron over the course of 30 minutes in simulated gastric fluid at pH 1.6; the composition releases less than 20 wt % of the total iron content as ferrous iron over the course of 30 minutes in simulated gastric fluid at pH 1.6; the composition releases less than 15 wt % of the total iron content as ferrous iron over the course of one hour in simulated gastric fluid at pH 1.6; the composition releases more than 10 wt %, 20 wt %, 30 wt % or 40 wt % of the total iron content over the course of one hour in simulated intestinal fluid at pH 6.6; and/or the composition releases more than 80 wt % of the total iron content over the course of 2 hours in simulated intestinal fluid at pH 6.6.

In one embodiment, the composition further comprises a stabilizer, such as ascorbic acid, ascorbate, or a combination thereof.

In one embodiment, the iron:protein ratio is 1:20 to 1:5.

In one embodiment, the composition consists of particles having an average particle size of 2000 microns or less, 1000 microns or less, 600 microns or less, 500 microns or less, or 300 microns or less, or 100 microns or less.

In one embodiment, the iron in the composition comprises at least 10%, 25%, 50%, 75%, 90%, 95%, 98% or 99% ferrous iron.

In one embodiment, the composition is more palatable than ferrous sulfate in acidified water.

In one embodiment, the composition is stable with respect to ferrous iron content and microbiological burden, for at least 6 months when stored in a sealed container at accelerated storage conditions (40° C. and 75% Relative Humidity).

In one embodiment, the composition is stable with respect to ferrous iron content when stored in a sealed container at ambient conditions for at least 24 months.

In one embodiment, the denatured protein comprises denatured whey protein, denatured whey protein isolate, denatured beta lactoglobulin, or combinations thereof.

DETAILED DESCRIPTION OF THE INVENTION

Figure 1:
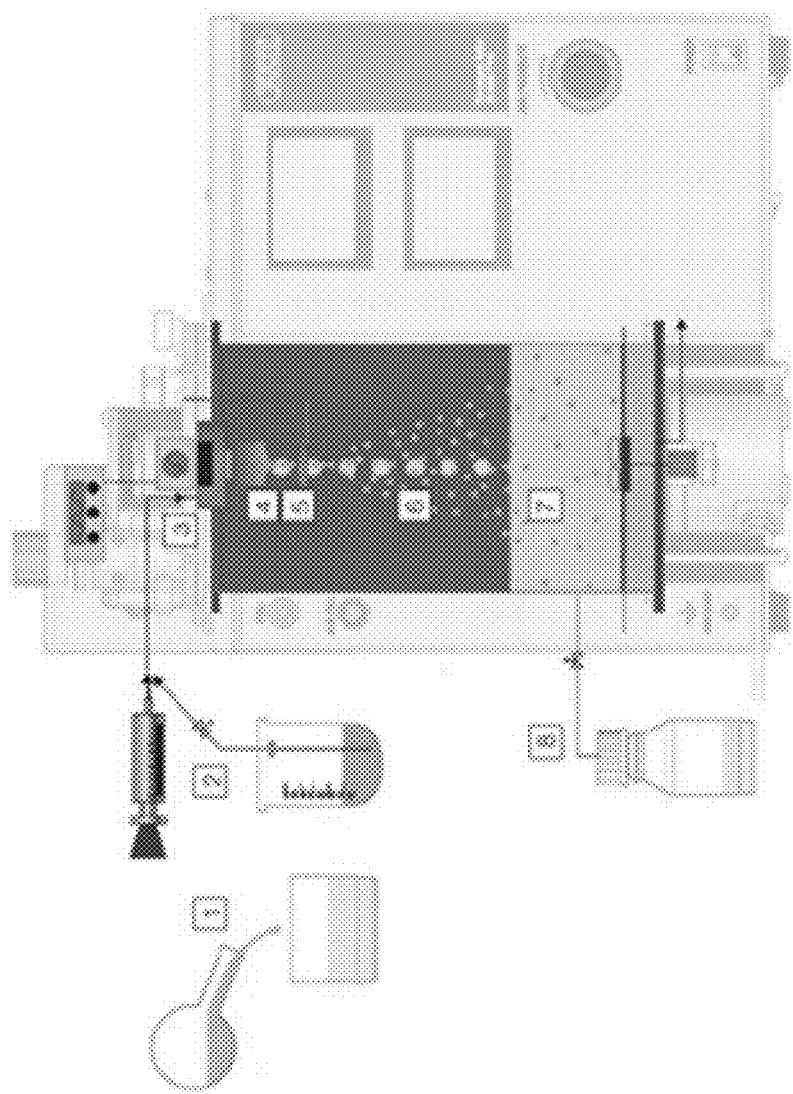
FIG. 1 shows one equipment setup used in accordance with aspects of an embodiment of the invention. First the protein solution is prepared as described above, pumped to a nozzle using either a syringe pump or air pressure system [2] with introduction of vibration (liquid or nozzle) [3] to form a droplet [4] which may have an electrostatic negative charge added [5] to aid dispersion and improve iron uptake into the bead. Control of droplet formation using e.g. flowrate and vibrational frequency is observed in the light of a stroboscopic lamp [6]. The bead is formed in the curing solution with iron, resulting in iron uptake into the bead and contributing to the bead gelation [7]. Finally, the gel bead is collected, washed and dried to form the amorphous dry bead.

As used herein, the term "calcium-depleted" or "decalcified" or "at least partially subjected to divalent metal ion removal" shall refer to protein raw material that has undergone a divalent metal ion removal process, including but not limited to the removal of calcium. Preferably, a decalcified protein comprises less than 200 mg calcium per 100 g protein, less than 100 mg calcium per 100 g protein, less than 50 mg calcium per 100 g protein, or only trace amounts of calcium. Alternatively, a decalcified protein may contain (excluding iron) less than 1% divalent metal ions (w/w), less than 0.5% divalent metal ions (w/w), less than 0.1% divalent metal irons (w/w), or only trace amounts of divalent metal ions. There are standard methods of de-calcification of protein, apparent to those skilled in the art, including (a) acidification with dialysis and/or ultrafiltration and/or diafiltration, and or (b) using calcium chelating/sequestering agent(s) and/or (c) using cation exchange methods.

The term "protein-based carrier" as used in this specification should be taken to mean a substance at least partially derived from a protein-based source that is combined with a form of iron into a composition. The carrier may be used to render the composition suitable for its intended purpose. The purpose may be the effective delivery of iron to a mammalian subject. The protein carrier may provide advantages to the composition. Examples of such advantages include, but are not limited to, providing an advantageous modified iron-release profile to the composition, conferring additional anti-oxidative effects to the composition, reducing the level of gastrointestinal discomfort resulting from administration of the composition, and improving the level of iron uptake.

As used herein, the term "denatured protein" means a protein that is at least partially denatured, i.e., at least 5% denatured.

As used herein "encapsulation" or "entrapped" means a process involving the complete envelopment (entrapment) of pre-selected material(s) within a matrix (usually referred to as a bead or sphere or microbead) or a core-shell capsule (usually referred to as a capsule), to give particles ranging from a few hundred nanometers up to a several centimeters in size.

"Bound iron", as used herein, refers to iron that is not easily washed off and "unbound iron" can be easily washed off. These terms are not intended to imply covalent or ionic bonding.

As used herein, the term "largely amorphous" means absence of evidence of short range order in the XRD associated with crystallinity. In other words, low crystallinity—See, e.g., FIG. 14.

As used herein, an "amorphous" substance includes a largely amorphous substance.

A capsule is made up of a defined and distinctive core (consisting of the encapsulated material) and shell part which are separated from each other. In preferred embodiments a microbead is a spherical structure which has (encapsulated) material distributed throughout the structure (i.e., a matrix). A microbead may have a surface layer ("skin") having the same composition as the interior but with different structure and chemical properties to the interior. The skin thickness and structure may influence microbead properties and behaviour—for example, swelling, pliability and payload diffusion.

Figure 2:
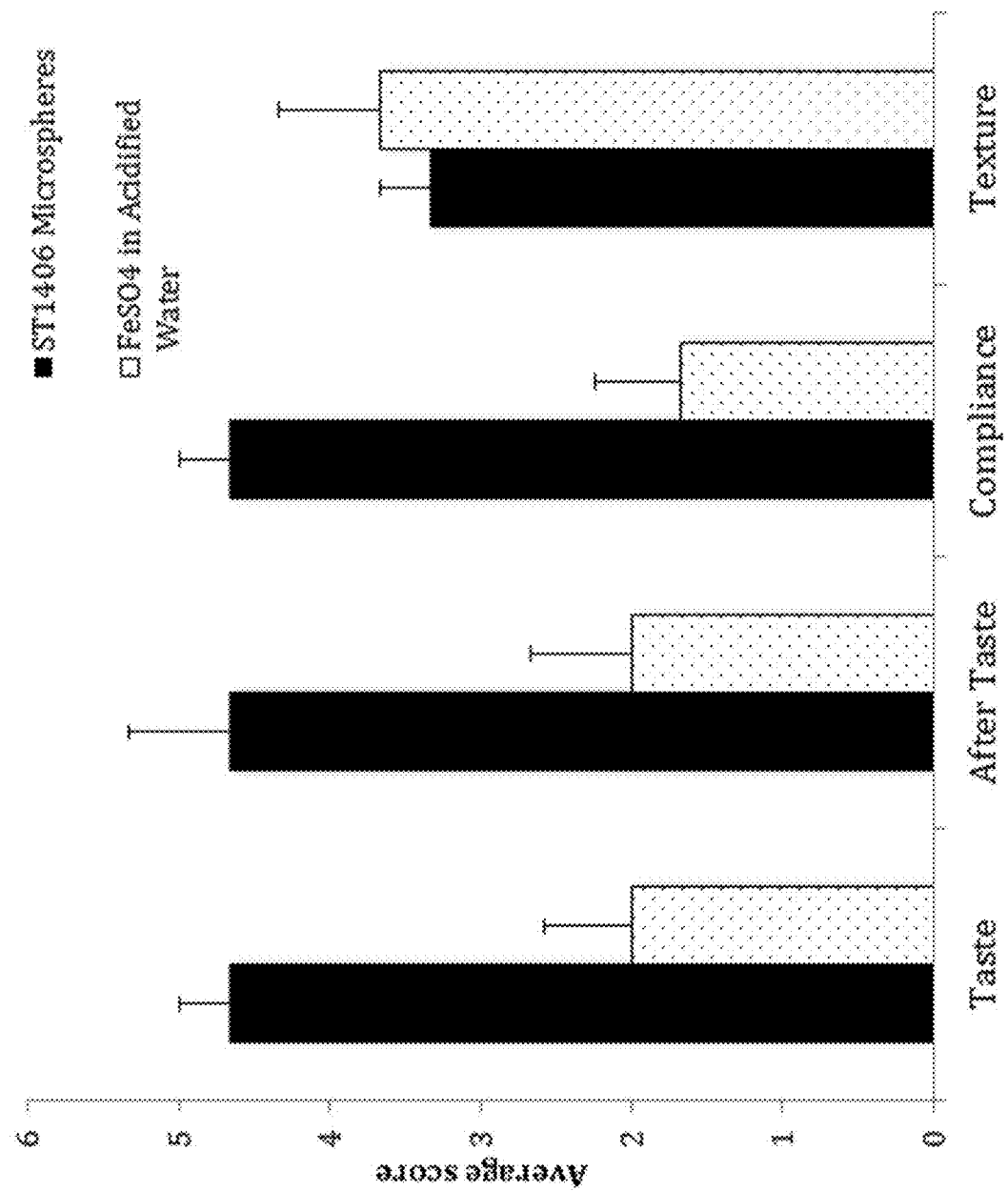
FIG. 2 depicts an example of the comparative palatability data for the ST1406 embodiment of the invention. The data show results from subjects (n=6) randomly allocated to aqueous dispersions of microbeads of the invention (ST1406) in apple juice (100 mL) in comparison with equimolar doses of ferrous sulfate in acidified water and apple juice (100 mL). The results show that the beads score highly on taste, after taste and compliance measures, all significantly greater (p<0.02) than ferrous sulfate in acidified water. On texture, there was no preference of either formulation on average, despite differences in formulation. Accordingly, beads prepared in accordance with the invention are significantly more palatable than FeSO4 in aqueous solution.
Figure 6:
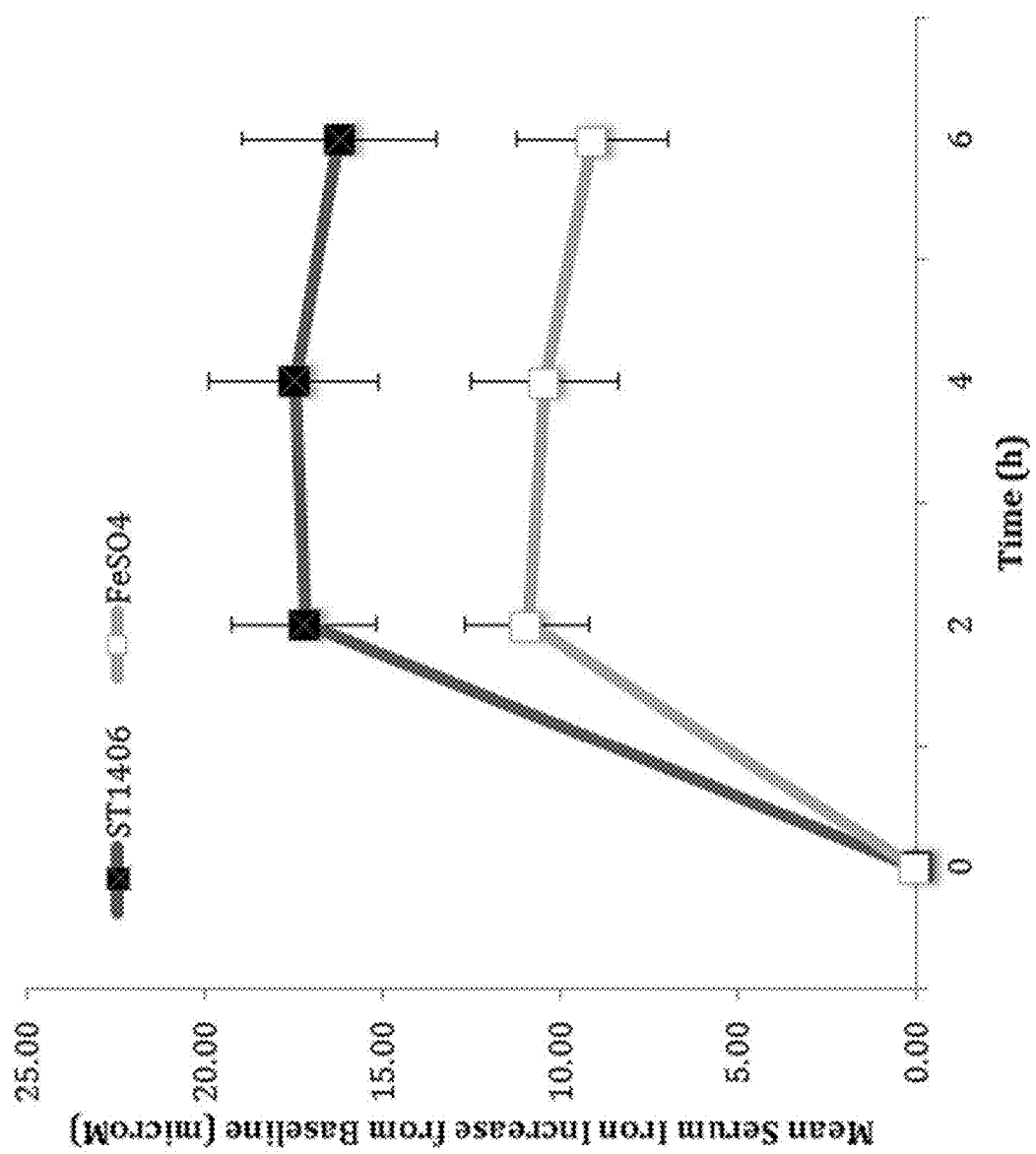
FIG. 6 depicts an example of the comparative serum iron curves of ST1406 microbeads of the invention and FeSO4 at equimolar iron dose in fasting subjects over 6 hours. The median Area Under the Curve 0-6 hr (μmol/L·hr) for serum iron with microbeads of the invention was 83.7 [IQR 97.5-72.5] compared to 42.1 [IQR 62.5-31.0] p=0.025 with FeSO4. The relative bioavailability of microbeads of the invention (n=8) was 199%±36% of FeSO4 over 0-6 hours, p=0.025. Detailed description of the methodology is described below. The primary endpoint in this study is serum iron Trough to Peak Ratio (TPD) over 0-6 hours and the median TPD for microbeads of the invention was 20.1 μmol/L [IQR: 16.1-21.7] while the value for FeSO4 was 9.7 μmol/L [IQR: 7.4-13.6], p=0.017.

The iron-containing microbeads of the invention release only a limited amount of ferrous iron in simulated gastric solution at low pH and yet when delivered to a mammal via the oral route, results in greater bioavailability of the iron in vivo compared to ferrous sulfate (FIG. 6). Additionally, preferred embodiments of the invention reduce adverse effects (FIG. 3) and improve palatability (FIG. 2). This provides a way of maintaining iron intake without experiencing the adverse effects of medicinal products. It provides a way of more effectively maintaining iron intake using a supplement without other adverse effects, such as poor palatability associated with iron intake.

Thus, in one embodiment, the invention provides a preparation of microbeads comprising discrete microbeads, in which the microbeads comprise iron and denatured protein. In one embodiment, iron is entrapped within a denatured protein matrix core having an aggregated denatured protein skin. Optionally, the skin may also contain a gelling agent, such as a complex carbohydrate, such as alginate, or a protein, such as gelatin.

Additional iron loading can be achieved by applying a negative charge on the surface of the microdroplet prior to curing in an iron solution or by varying the curing temperature or level of protein denaturation or by incorporating substances such as vitamin C (ascorbic acid) known to chelate iron.

In one embodiment, the protein in the protein matrix has been subjected to a divalent metal ion removal process that results in calcium depletion.

Suitably, the protein in the protein matrix comprises whey protein, another milk protein composition containing beta lactoglobulin, or pea protein. Preferably the protein is denatured whey protein or calcium depleted denatured whey protein.

In one embodiment, the microbeads comprise 0.1% to 10% iron (dry weight %). Preferably, the microbeads comprise 0.2% to 7%, 0.5% to 7.0%, 1% to 6%, 1% to 3%, 1% to 2%, 1% to 2.5%, or 2.5% to 10% iron. In another embodiment, the composition contains an iron content of up to 20% w/w, above 5% w/w, or between 5 and 10% w/w with respect to dry weight.

The percent iron can be estimated by instrumental or colorometric methods following digestion of the microbeads. Total residual inorganic content which reflects iron in calcium depleted microbeads can be estimated by high temperature thermogravimetric analysis. Alternatively, the microbeads preferably have a ratio of iron:protein ranging from about 1:1000 to about 1:7 or 1:5, about 1:500 to about 1:7 or 1:5, about 1:500 to about 1:10, about 1:200 to about 1:10, about 1:100 to about 1:7 or 1:5, about 1:100 to about 1:10, or about 1.2:100 to about 1:15, or other ranges of these ratios.

Typically, the iron in the microbeads contains ferrous (II) iron, which can be derived, for example, from ferrous sulfate, ferrous fumarate, ferrous gluconate, ferrous bisglycinate, ferrous taurate, ferrous citrate, ferrous ascorbate, ferrous chloride, ferrous nitrate, ferrous lactate, ferrous acetate, ferrous carbonate/siderite, ferrous oxides or iron amino acid or iron carbohydrate chelates or complexes. The composition of the invention may also contain ferric (III) iron or a mixture of iron II and iron III. The iron content of the composition preferably contains at least 10, 25, 50, 75, 90, 95, 98 or 99 wt % ferrous iron.

Preferably, the microbeads comprise acetate, citrate, phosphate, or ascorbate counterions. In preferred embodiments, these ions improve stability by reducing oxidation of the ferrous iron and/or improves release or taste characteristics.

The invention also provides methods for increasing bioavailable iron in a mammal, such as treating or preventing iron deficiency, comprising the steps of administering a composition according to the invention (preferably microbeads) to the mammal.

A composition according to the invention can be administered by any delivery vehicle known in the art. A preferred embodiment is an edible formulation, such as a powder (such as infant formula), prenatal vitamin formulation, multivitamin formulation, supplement, chewable supplement, gummy, food (such as chocolate or fat/oil), beverage, animal feed, tablet, capsule, or suspension. Lower-palatability embodiments are preferably in the form of capsules or coated tablets.

Compositions of the invention are preferably administered at a dosage sufficient to deliver an effective amount. One of ordinary skill in the art can determine the needs of a particular subject and take into account the bioavailability of the composition of the invention to determine an appropriate dosing regimen.

In one embodiment, beads are prepared by providing a carrier comprising denatured protein and iron; forming the carrier into microdroplets; curing the microdroplets into beads; and drying the beads until the moisture content of the beads is less than 10%, less than 7%, less than 5% or less than 3%, by weight.

In another embodiment beads are prepared by providing a carrier comprising denatured protein and optionally iron; forming the carrier into microdroplets; curing the microdroplets into beads in a curing solution containing iron; and drying the beads until the moisture content of the beads is less than 10%, less than 7%, less than 5% or less than 3%, by weight.

Preferably, the beads have a denatured aggregated protein skin.

If the microdroplets are cured by dropping them into a curing solution containing iron, in addition to iron, the curing solution may contain monovalent ions such as sodium in the range 100-1000 mM. Suitable sodium salts include sodium acetate, sodium chloride and sodium sulfate. The curing solution may also contain surfactants for example tween. The pH of the curing solution may be modified by introducing HCl or acetic acid or ascorbic acid in order to promote protein aggregation (curing of the microbead). Additional iron uptake into the microbead and improved shape can be achieved by applying a negative charge on the surface of the microdroplet prior to curing for example by using an electrostatic charging device.

Preferably the curing solution contains an organic acid such as acetic acid, which influences aggregation and curing (protein aggregation) through modification of the pH and, by transferring counter ions onto the protein side chains. The presence of the acetate or comparable counter ions may be detected in the resulting microbeads by techniques such as infra-red spectroscopy.

The cured beads can be washed to remove unbound or weakly bound iron prior to drying. The washing may be performed using deionized water or by using aqueous solutions of acetate buffer, citrate or sodium ascorbate, for example. More washing will generally decrease the amount of iron in the composition.

Drying is preferably done in an oven at 50-100° C., preferably at about 80° C. Alternatively, drying can be done at lower temperatures, such as room temperature, under vaccum. Preferably the drying is performed under an atmosphere of nitrogen or argon.

In another embodiment, drying occurs between 15° C. and 80° C., between 25° C. and 60° C., or at room temperature. In some embodiments, the step of drying may be performed under atmospheric pressure. In other aspects of some embodiments, the step of drying may be performed in at least a partial vacuum.

In aspects of some embodiments, the drying step results in the loss of between 40% and 90% of total weight of the composition, or between 70-80% of total weight of the composition.

Drying can be performed in a rotating drum dryer under vacuum to reduce exposure to atmospheric oxygen while keeping particles in a constant motion to prevent sticking of the drying particles. Other techniques used for drying include using a vibrational fluidized bed dryer or rotary evaporator devices, which allow drying under controllable atmospheric conditions will keeping the particles in motion. Drying can also be performed by supplying a constant airflow or nitrogen flow over the microbeads.

In one embodiment, the invention relates to a preparation of microbeads in which the microbeads comprise a polymerized matrix formed from denatured calcium depleted protein having iron microencapsulated and/or entrapped within the matrix.

Typically, the microbeads have a generally spheroid shape. In some embodiments the mean diameter is 2000 microns or less, 1000 microns or less, 600 microns or less, 500 microns or less, or 300 microns or less. In some embodiments, the particle size distribution is narrow.

In some embodiments particles have a diameter of between 0.2 and 4000 microns. The particles may be in the form of beads with a particle size between 0.2 and 4000 microns, between 50 and 2000 microns, between 150 and 1000 microns, or between 300 and 600 microns in diameter. In some embodiments beads over a certain size may be preferable because they may display better flow characteristics, reducing the likelihood of aggregation during handling and the need for the use of an anti-caking agent or the like. Alternatively, the particles may be nanoparticles with a size below 0.2 microns.

The composition could comprise particles per se, or the composition could comprise the end result of such particles that have undergone one or more additional processing steps. This can be advantageous because in use, the protein may form a protective coating around the outside of the bead. This may result in a staged-release profile.

Microbead size can be varied within a certain range by regulating the frequency of vibration and/or the flow rate of the protein solution with higher frequencies and lower jet velocities enabling the generation of smaller whey protein droplets. The main factor governing iron microbead size in the embodiments of the invention exemplified herein is the nozzle diameter, either single or concentric, whereby the final dry microbead diameter is approximately 1.25× the size of the chosen nozzle, using this specific technique.

In some embodiments, the microbeads of the invention are treated with acetate, citrate, (such as tri-sodium citrate), or a phosphate (such as di-sodium phosphate) or ascorbate.

The microbeads of the invention can be made by extruding the calcium depleted denatured whey protein suspension into a curing solution containing ferrous iron. In one embodiment a calcium depleted denatured whey protein solution/suspension is extruded using prilling through a nozzle to form a laminar jet in which break-up of the extruded laminar jet results in the formation of microdroplets. Preferably, these droplets are rapidly cured while maintaining their shape and avoiding high net positive surface charge. The microdroplets are preferably cured at elevated temperature, at low pH and high ionic strength produced by ferrous iron, sodium and sulfate ions. The microbeads of the invention are preferably dried at elevated temperature, preferably in a nitrogen atmosphere. The resulting microbeads preferably have <10% moisture as indicated by thermogravimetric analysis.

In another embodiment, a ferrous iron containing solution is prepared and separately a calcium depleted denatured whey protein suspension is prepared. Preferably, the solution and suspension are delivered to a vibrating nozzle, in which the solution and suspension are admixed at or just prior to the nozzle and simultaneously extruding the admixed solution and suspension through the vibrating nozzle to form a laminar jet in which break-up of the extruded laminar jet into microdroplets is induced by applying a sinusoidal frequency with defined amplitude to the nozzle. Preferably, the microdroplets are cured immediately in a curing solution to prevent oxidation and generate the microbeads comprising the ferrous iron entrapped within a crosslinked calcium depleted denatured whey protein matrix.

Preferably, the method includes an additional step of immersing the microcapsules in water or similar washing approach to reduce the unbound iron load. The microbeads may also be washed with a buffer comprising an acetate, citrate, phosphate or ascorbate such that the resultant microbeads are coated with an acetate, citrate, phosphate or ascorbate.

One embodiment of the invention is a composition comprising iron and a carrier comprising denatured protein. The iron in the composition preferably comprises at least 10%, 25%, 50%, 75%, 90%, 95%, 98% or 99% ferrous iron. The denatured protein preferably comprises whey protein, whey protein isolate, beta lactoglobulin, or combinations thereof. Preferably, the denatured protein is at least 5% denatured. In one embodiment, the denatured protein contains at least 5% denatured beta lactoglobulin. The iron:protein ratio, by weight, is preferably about 1:1000 to about 1:10. Preferably the microbeads of the invention are dried at ambient pressure under nitrogen or argon. Preferably, the composition releases less than 50 wt % of the total iron content as ferrous iron over the course of one hour in simulated gastric fluid at pH 1.6; or less than 50 wt % of the total iron content as ferrous iron over the course of 30 minutes in simulated gastric fluid at pH 1.6; or less than 20 wt % of the total iron content as ferrous iron over the course of 30 min in simulated gastric fluid at pH 1.6; or less than 15 wt % of the total iron content as ferrous iron over the course of one hour in simulated gastric fluid at pH 1.6. Preferably, the composition releases more than 10 wt %, 20 wt %, 30 wt % or 40 wt % of the total iron content over the course of one hour in a solution at pH 6.6 containing representative digestive enzymes and representative ionic strength and bile acid composition. The release rates are based on the testing methodology described herein.

Preferably, the composition, when administered orally to a human, has a bioavailability at least 20%, 30%, 40% or 50% greater than that of an equal dose of an orally administered solution of ferrous sulfate in acidified water or a relative bioavailability of at least 120%, 130%, 140% or 150% that of an equimolar dose of an orally administered solution of ferrous sulfate in acidified water. Bioavailability is based on the testing methodology described herein for measuring serum iron AUC.

Preferably, the moisture content of the composition is less than 10% by weight, less than 7% by weight, about 3-10%, about 3-7%, or about 5-7%.

Figure 11A:
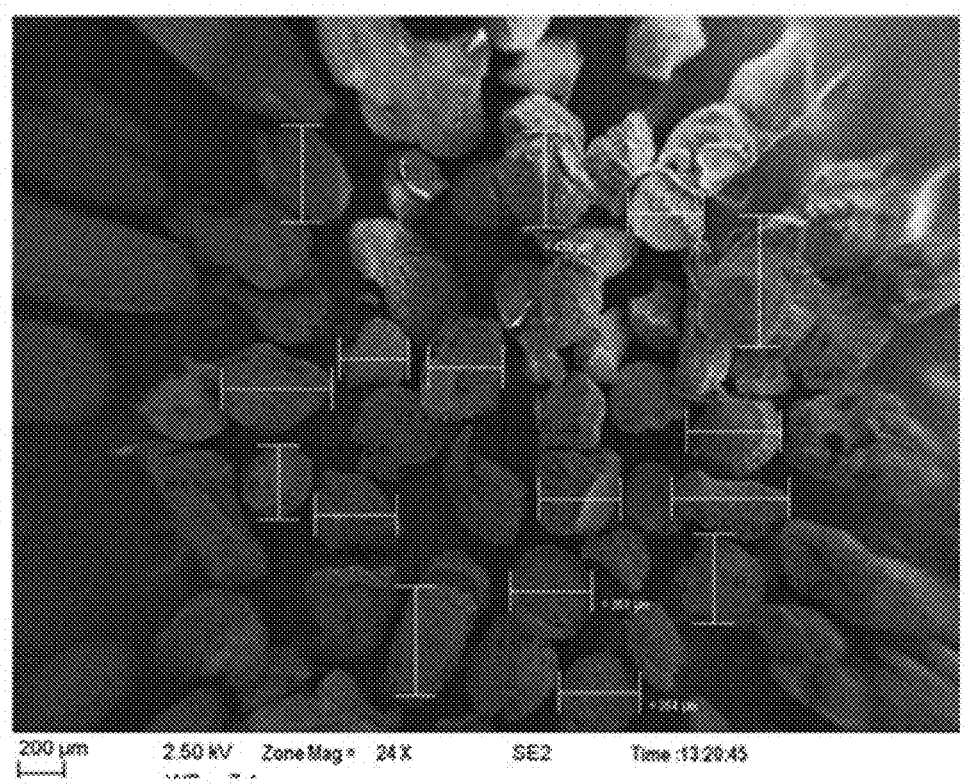
FIG. 11(A) depicts a low magnification SEM of an example of the microbead of the invention. (B) shows a zone close to the surface of the microbead. This is an example where folding of the skin has occurred during the drying process associated with the microbead volume reduction-shrinkage. (C) shows a further magnified zone close to the surface of the microbead with the fibrillary features associated with iron-mediated protein aggregation.
Figure 11B:
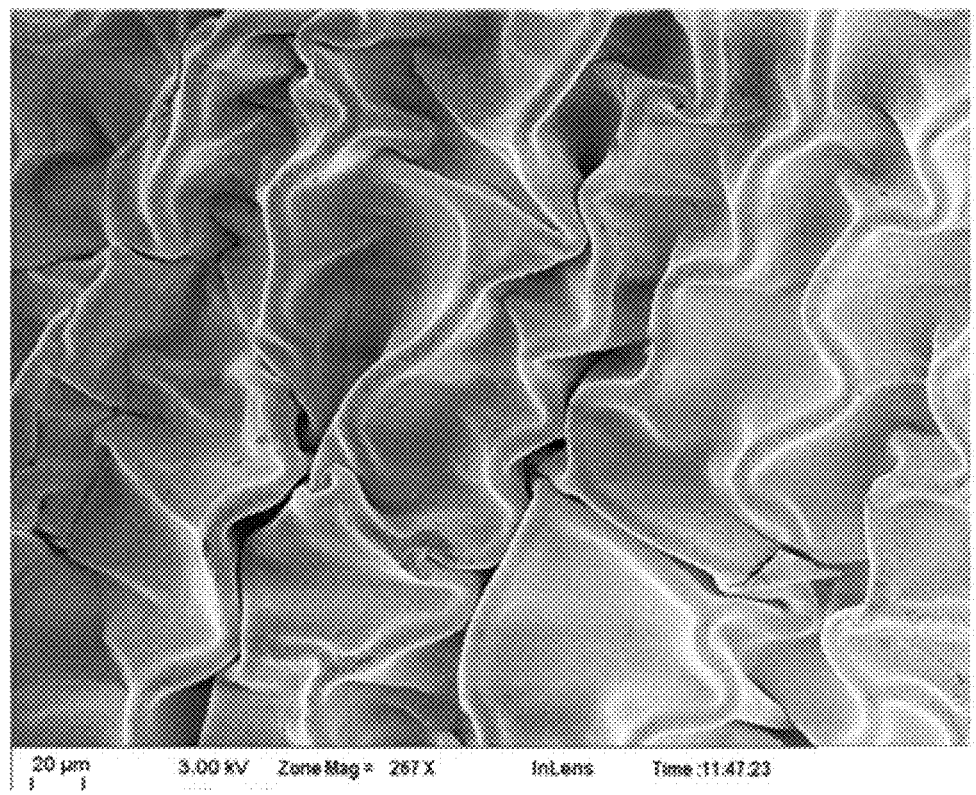
Figure 11C:
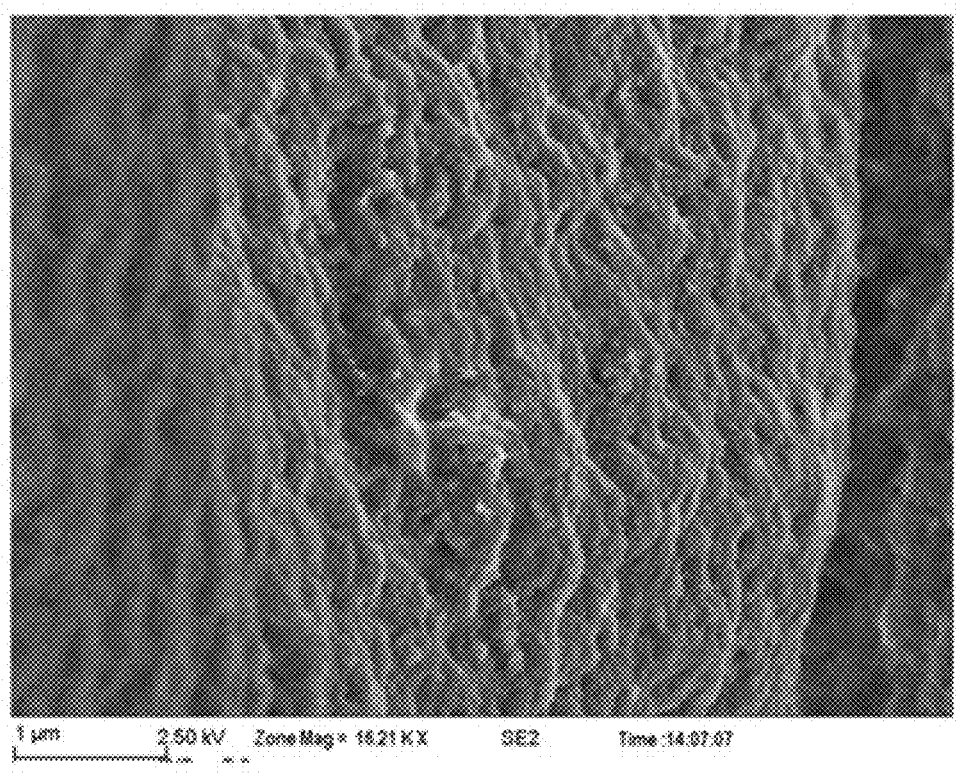
Figure 12:
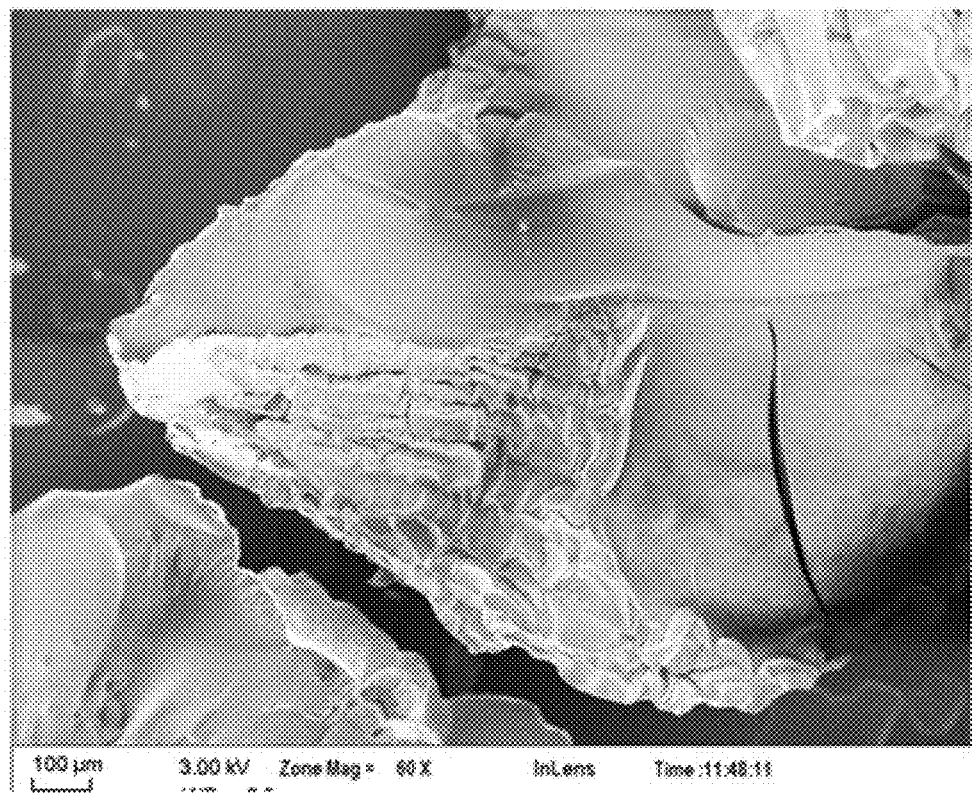
FIG. 12 depicts a low magnification SEM of an example of the microbead of the invention which have been mechanically fractured to provide a cross-sectional view of the matrix and skin. The scanning electron microscopy (SEM) images were recorded on a Zeiss Ultra Plus Field Emission SEM with a Gemini® column (Zeiss). The dry sample beads were placed on a conducting carbon tape without any further preparation or sample coating. Accelerating voltages between 2-3 kV was used to overcome the extensive discharge effect.
Figure 13:
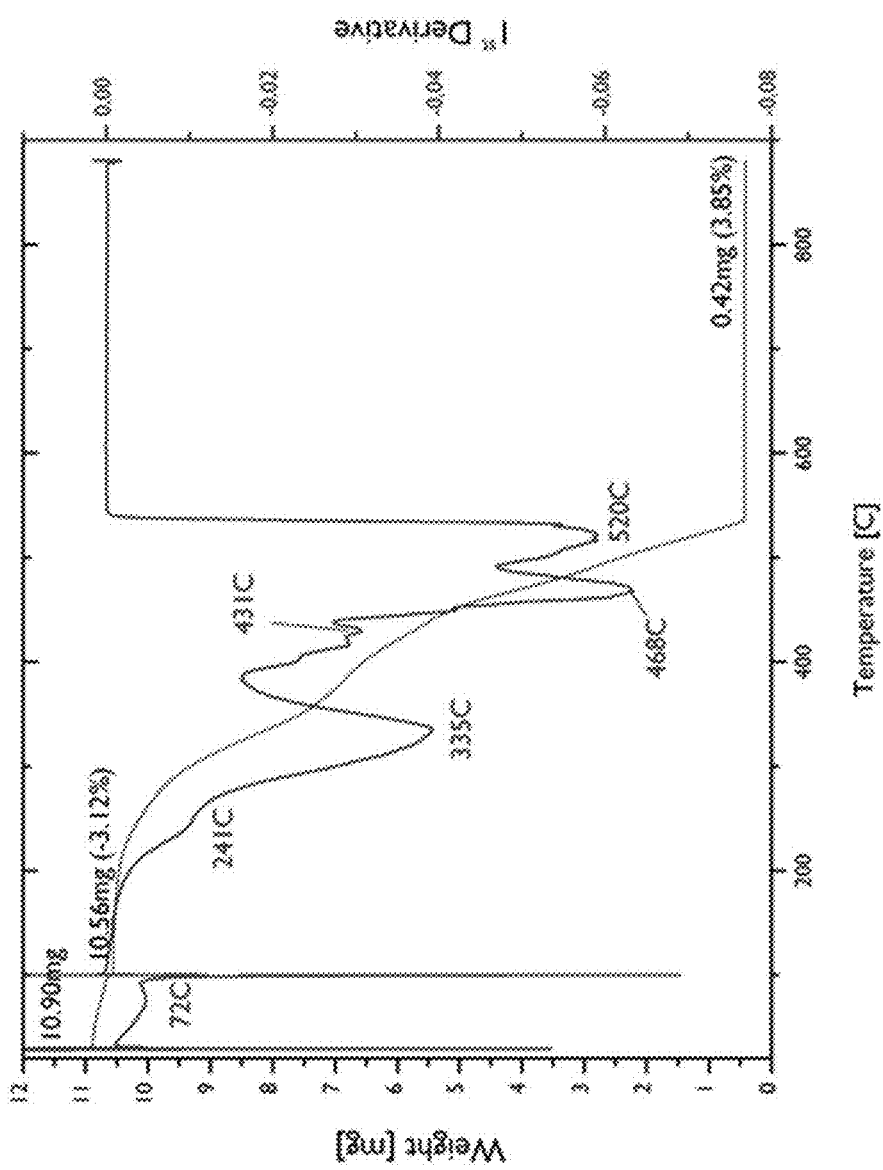
FIG. 13 depicts thermogravimetric analysis (TGA) of microbeads of the invention. Experiments were conducted on a Pyris 1 Thermogravimetric Analyser (Perkin Elmer). Weighed, powdered samples (10-15 mg) were analysed in open ceramic pans. All samples were measured under the following temperature program: isothermal at 30° C. for 5 min; gradient from 30° C. to 100° C.; isothermal at 100° C. for 20 min; gradient from 100° C. to 900° C. at 10° C./min rate and under air purge. Sample water content is calculated from the weight difference at the end of the 100° C. isotherm and the initial sample weight.
Figure 14A:
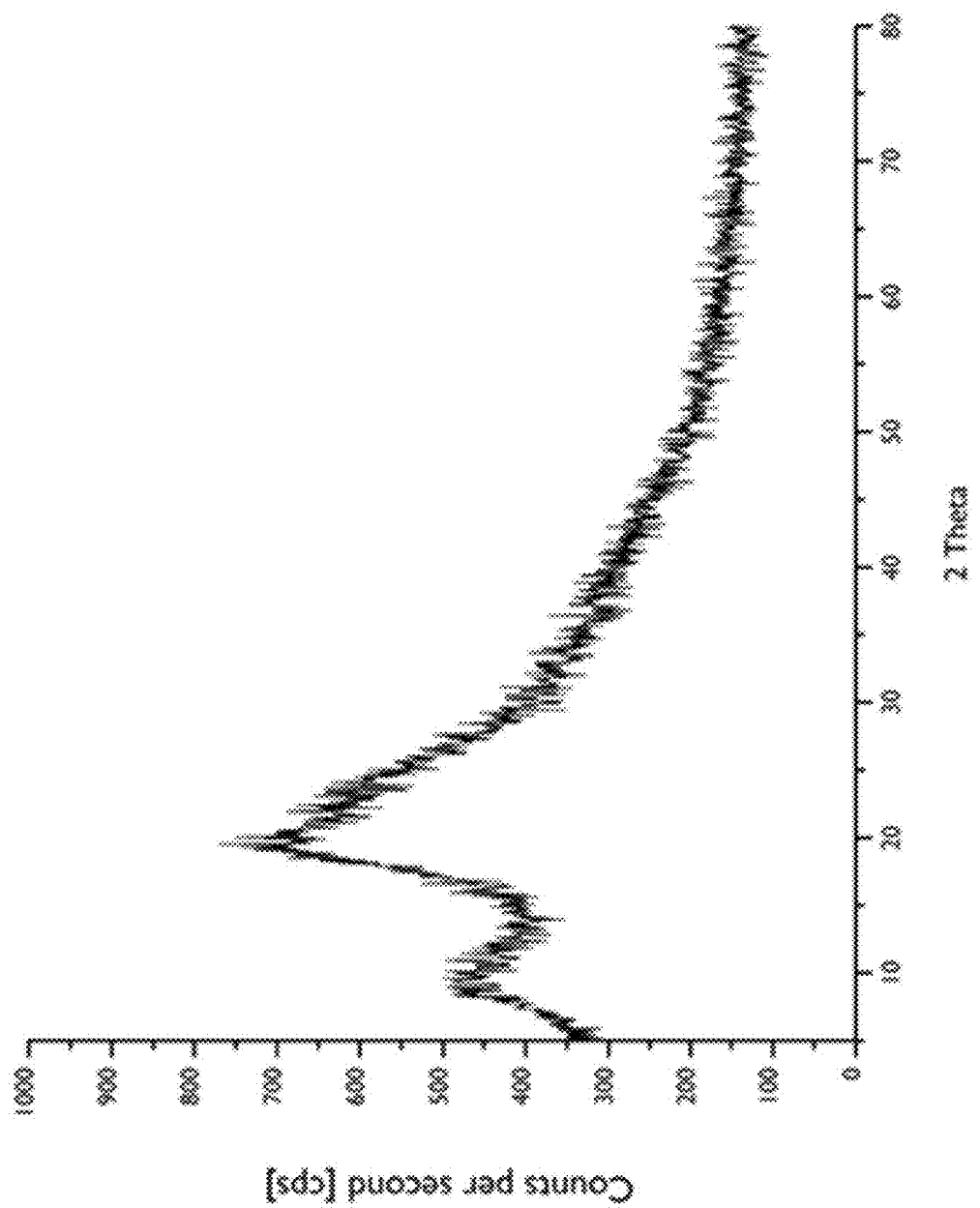
FIG. 14a depicts an X-Ray Diffraction profile of calcium depleted denatured whey protein showing a largely amorphous profile. PXRD measurements were performed on samples placed on a low background silicon sample holder, using a Rigaku Miniflex II desktop X-ray diffractometer (Rigaku, Tokyo, Japan). The PXRD patterns were recorded from 5° to 80° on the 2θ scale at a step of 0.05°/s. Xray tube composed of Cu anode (λCuKα01.54 Å) was operated under a voltage of 30 kV and current of 15 mA. The broad baseline peaks however reflect low level order in the protein structure.
Figure 14B:
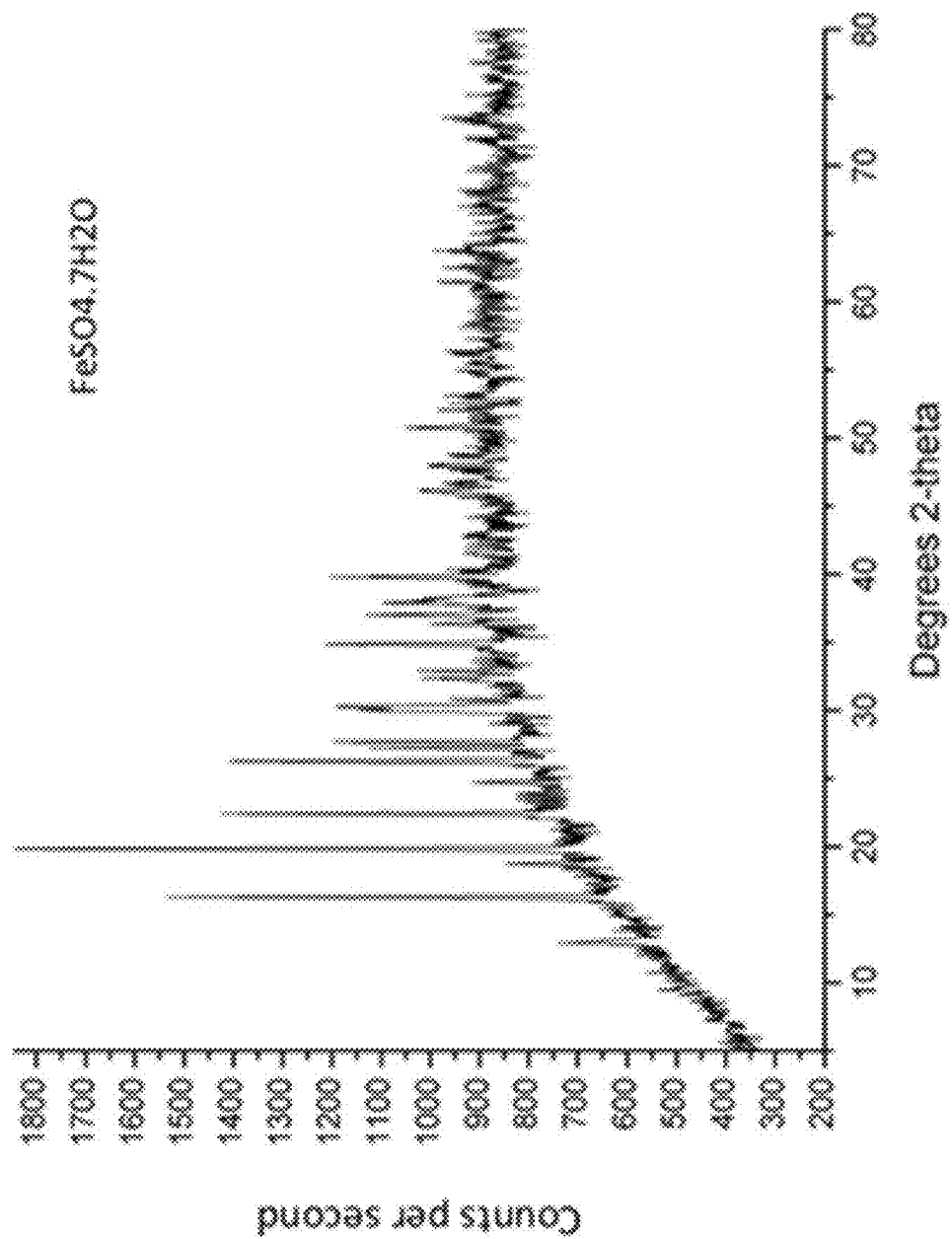
FIG. 14b depicts an X-Ray Diffraction profile of ferrous sulfate heptahydrate showing evidence of crystallinity.
Figure 14C:
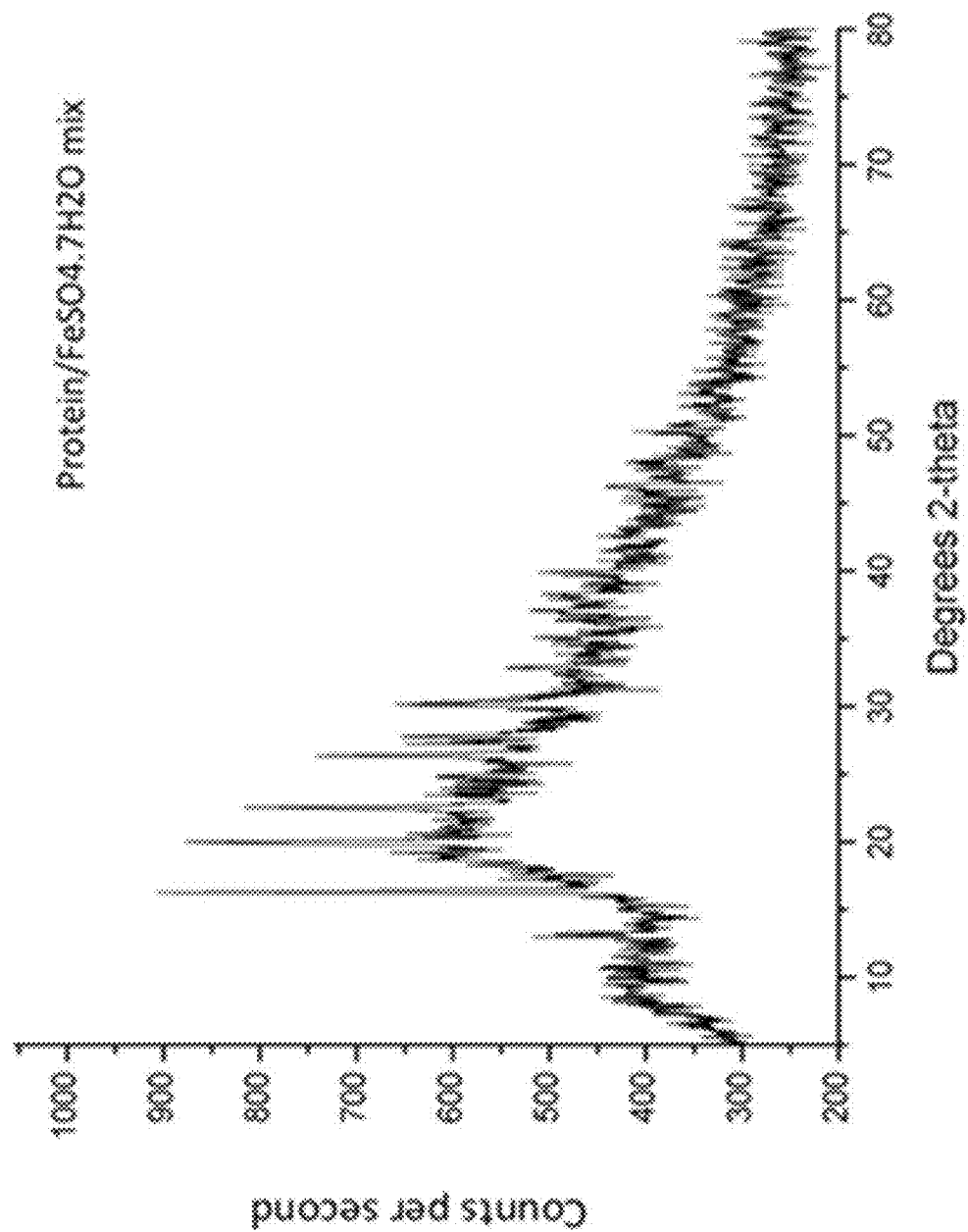
FIG. 14c depicts an X-Ray Diffraction profile of calcium depleted denatured whey protein physically mixed with ferrous sulfate heptahydrate showing evidence of crystallinity.
Figure 14D:
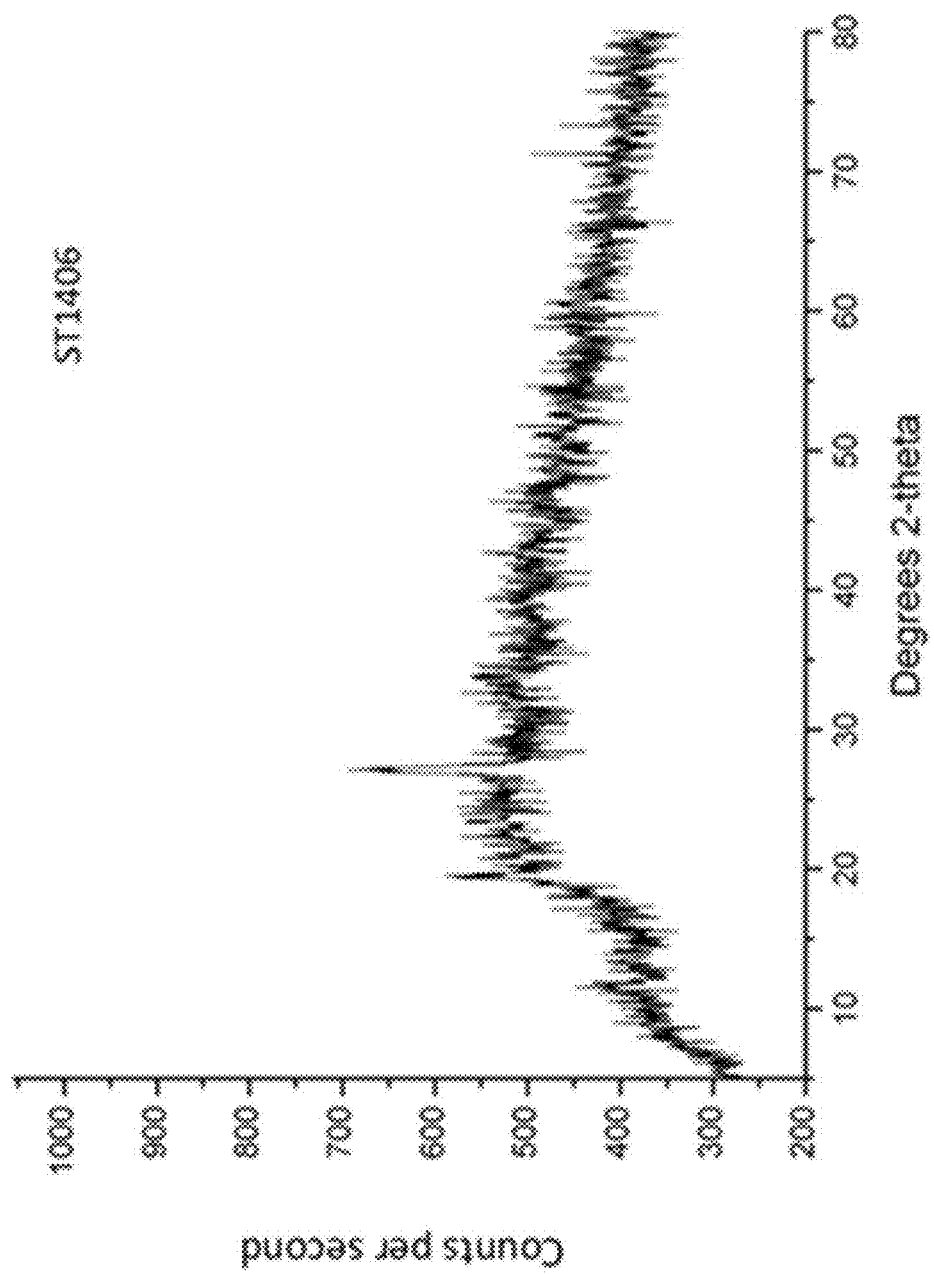
FIG. 14d depicts an X-Ray Diffraction profile of ST1406 microbeads of the invention with the same iron/protein loading as the physical mixture (FIG. 14b) and is largely amorphous. There are no typical PXRD peaks present which are associated with crystalline Iron(II) sulfate.

Preferably, the carrier comprises a matrix of denatured aggregated protein. In a preferred embodiment, a matrix microbead structure forms upon the microdroplet (such as upon entering the low pH iron solution) that causes rapid aggregation and curing on the outer surface of the particle, producing a skin on the microbead whose characteristics can influence diffusion and degradation rates in the intestine. See, for example, FIGS. 11 and 13.

In one embodiment, the composition comprises a stabilizer, such as Ascorbic acid, or Ascorbate (Sodium ascorbate, Calcium ascorbate, Fatty acid esters of ascorbic acid), Tocopherols (Alpha-tocopherol, Gamma-tocopherol, Delta-tocopherol), Propyl gallate, Octyl gallate, Dodecyl gallate, Erythorbic acid, Sodium erythorbate, Tertiary-butyl hydroquinone, Butylated hydroxyanisole (BHA), Butylated hydroxytoluene (BHT), or combinations thereof.

In a preferred embodiment, the composition is more palatable than commercially available iron formulations, such as ferrous sulfate in acidified water.

In a preferred embodiment, the composition is stable in that its dissolution profile at pH 1.6 and pH 6.6 changes less than 20%, less than 15%, less than 10%, less than 5% or is substantially unchanged with respect to iron II release for at least 6 months, preferably at least 2 years, when stored in a sealed container at ambient conditions. In a preferred embodiment, the composition is stable with respect to microbiological burden for at least 6 months, preferably at least 2 years, when stored in a sealed container at ambient conditions. Stability with respect to microbiological burden means the composition is "free of objectionable microorganisms", as that phrase is interpreted by FDA of 21 CFR 211.165.

Preferably, this includes a Total Viable Count with a Maximum Tolerable amount of $10^3$ cfu/1000 mg, Total Yeast and Moulds Maximum Tolerable $10^2$ cfu/1000 mg, and an absence of *E-Coli*.

In preferred embodiments, the composition is in the form of microbeads for oral administration. Preferably, after oral administration the incidence of constipation, as assessed using the Bristol Stool Scale (described herein), is reduced by at least 50% and/or the incidence of nausea, as assessed using the modified Gastrointestinal Symptom Rating Score (described herein), is reduced by at least 50%. See FIG. 3.

The term "calcium depleted" as applied to a composition should be understood to mean that the composition comprises less than 100 mg % (100 mg per 100 g protein dry wt %) of calcium. In some embodiments, the composition contains less than 0.1% or only trace amounts of calcium measured by standard methods.

Microbeads size can be varied within a certain range by regulating the frequency of vibration and/or the flow rate of the protein solution with higher frequencies and lower jet velocities enabling the generation of smaller whey protein droplets. The main factor governing iron microbead size in the embodiments of the invention exemplified herein is the nozzle diameter, either single or concentric, whereby the final microbead diameter is approximately 1.25× the size of the chosen nozzle, using this specific technique.

Breakup of the jet can be monitored using a stroboscopic lamp (e.g. FIG. 1) placed directly behind the protein droplet chain providing visualization of individual protein-iron drops during breakup. Droplet coalescence in the laminar jet stream will result in loss of monodispersity of iron microbeads. It is helpful for the formation of droplets if the protein is substantially negatively charged in solution. In the case of whey protein the solution pH should be above 5.2.

In certain embodiments, microbeads of the invention comprise (as a dry weight %): 75-95% or 85-95% denatured, optionally calcium depleted, whey protein or whey protein isolate; and 0.1-10.0% iron.

The denatured whey protein may, for example, be a denatured whey protein concentrate or denatured whey protein isolate. Methods for denaturing whey protein will be known to those skilled in the art, and include heat denaturation and pressure-induced denaturation. In one embodiment of the invention, the whey protein is heat denatured at a temperature of 70° C. to 140° C., preferably about 80° C. The whey protein is heated at a temperature of greater than 70° C. for more than 15 minutes. Usually, the whey protein is agitated during denaturation. Several methods for monitoring the unfolding/denaturation and formation of soluble oligomers will be known. These include dynamic light scattering and size exclusion techniques. It is useful to monitor the extent of thiol exposure in whey protein solutions using 5,5'-dithiobis-(2-nitrobenzoic acid) or DTNB which produces coloured adducts on reaction with exposed thiols. In a preferred embodiment, the extent of denaturation of the protein or beta lactoglobulin is greater than 80% or greater than 90%, which can be measured using DTNB.

In some embodiments, the protein employed in the process of the invention has at least 90%, 94% or 98% protein content (on a moisture, carbohydrate and fat free basis).

Suitably, the concentration of the at least partially denatured protein solution/suspension is from 4 to 30%, preferably from 7 to 30%, and ideally from 9 to 16% (w/v). Typically, the protein is whey protein, ideally, the suspension is passed through a series of filters having a gradually decreasing pore size.

Examples of iron salts include ferrous sulfate, ferrous fumarate, ferrous gluconate, ferrous bisglycinate, ferrous taurate, ferrous citrate, ferrous ascorbate, ferrous chloride, ferrous nitrate, ferrous lactate, ferrous acetate ferrous carbonate/siderite ferrous oxides. Ferric forms of these salts as well as ferric sodium diphosphate, ferric ammonium citrate and ferric chloride.

In other embodiments, the composition could contain or be prepared with ferric and/or ferrous ion complexes or salts in anhydrous or hydrated states containing for example sulfate, phosphate, folate, acetate, propionate, maleate, benzoate, salicylate, fumarate, glutamate, aspartate, citrate, lactate, succinate, tartrate, glycollate, hexanoate, octanoate, decanoate, oleate, stearate, bisglycinate, fumarate, gluconate. These iron complexes and salts used could also be different iron oxides, oxide-hydroxides or hydroxides. The composition could be prepared with iron salts in mixed oxidation states, and their hydrates.

In one embodiment, the ferrous iron solution has a pH of less than 5 or less than 4.5.

The curing solution is typically free of calcium ions. The curing solution has a sodium concentration of 0.1-1M or typically 0.2-0.5M. Suitably, the solution has an organic acid concentration of 0.1 to 0.6M, typically 0.15 to 0.25M, and ideally about 0.2M. Typically, the solution has a pH of 3 to 4.5, suitably less than 4. Generally, the solution has a temperature of 20-65° C., typically about 45° C. Typically, the acidic curing solution comprises a surfactant to prevent or inhibit agglomeration of the formed microbeads. Suitably, the surfactant is a polysorbate surfactant, ideally Tween 20.

Suitably, the formed microbeads are subject to an extended curing period in the curing solution, for a period of at least 15 minutes (after gelation), and preferably for a period of at least 20 minutes. In a preferred embodiment of the invention, the formed microbeads are cured for a period of time from 20 to 180, 20 to 120, or 20 to 60 minutes. Ideally, the curing solution is agitated during the curing process.

The microbeads of the invention are typically capable of surviving intact during passage through the mammalian stomach and capable of releasing the ferrous iron in the gastrointestinal tract distally of the stomach, for example in the small intestine. The term "surviving intact in the stomach" means that the microbeads are resistant to gastric and peptic break-down in the mammalian stomach during gastrointestinal transit.

In certain embodiments, the microbeads of the invention are treated with acetic acid, citric acid, ascorbic acid solutions or their salts or phosphate solutions, which further improves ferrous stability and bioavailability in some embodiments. In some embodiments, the ascorbate or citrate or phosphate solution has concentration of 0.2 to 0.4M, 0.25 to 0.35M, or about 0.25M. Typically, the acid washing solution has a pH of 3-4, or 4 to 4.5 to 5.5.

A preferred method of producing the microdroplets is a prilling by vibration technique, in which the denatured calcium depleted protein and iron salt are prepared separately and not mixed until just prior to or during extrusion through a nozzle and laminar break-up of the extruded laminar jet is induced by applying a sinusoidal frequency with defined amplitude to the nozzle with defined aperture size. Examples of vibrating nozzle machines are the ENCAPSULATOR (BUCHI Labortechnik AG, Flawil, Switzerland), a machine produced by Nisco Engineering AG, or equivalent scale-up version such as those produced by BRACE GmbH and the like.

Typically, the nozzle has an aperture of between 60 and 2000 microns, preferably between 100 and 500 microns, suitably 140 and 300 microns, and ideally about 150 microns.

Suitably, the frequency of operation of the vibrating nozzle is from 100 to 20,000 Hz. Optionally an electrostatic potential is added to the droplet, wherein the electrostatic potential between nozzle and curing solution is typically 0.15 to 0.3 V. Suitably, the amplitude is from 4.7 kV to 7 kV. Typically, the falling distance (from the nozzle to the acidification bath) is less than 50 cm, preferably less than 40 cm, suitably between 20 and 40 cm, preferably between 25 and 35 cm, and ideally about 30 cm. The flow rate of suspension (passing through the nozzle) is typically from 3.0 to 20 ml/min; an ideal flow rate is dependent upon the nozzle size utilized within the process.

In one embodiment, the process involves a step of monitoring the size of the initial microbeads generated for suitability.

Suitable compositions include comestible products such as food products and beverages, and food supplements in any form, for example unit dose products, powders, and the like. Typically food products include health drinks, yoghurts and yoghurt drinks, health bars, and the like. The composition may be a component of a formulation which is edible and orally active, e.g as an infant formula powder, prenatal vitamin, multivitamin, supplement, chewable supplement, gummy, food, beverage, animal feed, tablet, capsule, or suspension.

The preparation of microbeads of the invention may be provided in a dried form, for example a spray-dried, drum dried, dehydrated, or freeze dried form, or they may be provided as a suspension is a suitable solvent, for example water.

Denatured calcium depleted whey protein isolate (WPI) is preferable for producing microbeads of the invention. Whey protein concentrate (WPC) is also a possible encapsulation material.

One aspect of this technology involves the use of denatured calcium depleted whey protein isolate/concentrate. In some embodiments, reducing the divalent metal content of protein raw material reduces spontaneous gelation of the protein solution during processing, enhances its iron binding characteristics and reduces calcium release following administration to mammals, therefore enhancing iron uptake. Calcium competitively inhibits iron uptake through DMT-1.

Dried calcium-depleted WPI is suitably dissolved in the optimum composition for iron microencapsulation. Calcium depleted whey protein isolate (WPI) can be initially denatured at appropriate environmental conditions (pH, salt, solid concentration) to enable the production of a soluble dispersion of protein aggregates suitable for extrusion and encapsulation in the presence of sodium acetate and ferrous sulfate. This process can be used to stabilize ferrous compounds in the matrix network of whey protein microspheres. This process occurs instantaneously when whey protein droplet comes into optimal conditions of electrolyte concentration, pH, agitation and temperature. Ferrous and sulfate ions in the curing solution can aid curing and allow iron uptake into the bead through diffusion and entrapment.

The preparation of calcium depleted whey protein (e.g., WPI) to form ferrous encapsulation material typically involves:

1. Dispersion of calcium depleted WPI in water with concentrations in the range of 4-30% (w/w), between 7-30% (w/w), or between 9-16% (w/w). This may be achieved, for example, using high shear stirring in a blade mixer or Ultra-Turrax in the range of 0.01-0.1% (w/w), preferably in the range 0.04-0.09% w/w), with a pH in the range of 5.0-9.0, preferably in the pH range 6.0-7.0. A small amount of iron may be added at this stage to improve droplet viscosity/surface tension.

2. Application of filtration to remove any denatured material with filtration pore size of <200 microns.

3. Application of heat treatment to induce protein denaturation (unfolding). Protein denaturation is suitably performed between 60-140° C., preferably between 70-121° C. at pH in the range of 5.0-8.5, preferably in the range of 6.0-8.2.

The calcium depleted denatured protein suspension can be extruded through a concentric nozzle with a ferrous sulfate solution into a curing solution containing acetic acid/sodium acetate (0.1-5 M) buffering system with a pH 3-4.5, with surfactant and continuous agitation to reduce coalescence/aggregation at high flow rates. It will be understood that bringing the pH of the denatured protein solution close to its isoelectric point ("PI") will promote aggregation by reducing repulsive coulombic forces.

A number of techniques can be used to obtain the microbeads of the invention. For simplicity the methods can be categorized as mechanical, chemical or physicochemical processes and include techniques such as: chemical; in-situ polymerization and interfacial polymerization; physiochemical; complex coacervation and mechanical; spray-drying and extrusion based methods.

Mechanical techniques are based on the principle of generating droplets from a polymer extruded through a nozzle (orifice) or from the breakup of a liquid jet. They work using mechanical means (i.e. cutting or vibration forces) to increase the normal dripping process at the orifice, or they break-up an extruded liquid stream produced by the polymer when it is passed through the nozzle. After production, the droplets are immediately solidified to spheres/capsules by either physical e.g. cooling or heating, or chemical means e.g. gelation. Several different mechanical based technqiues can be used to encapsulate iron and and other materials within whey protein matrices to produce particles with the final desired characteristics. Simple dripping is the oldest technology for the production of particles. The extrusion of a whey protein solution through an orifice (nozzle) at low velocities results in the extruded liquid sticking to the edge of the nozzle until gravitational force is high enough to overcome surface tension, resulting in the release of a drop. A small rise in the velocity increases the number of droplets formed, whilst further escalation amplifies droplet formation even further. After formation the droplets are immediately cured and the size of the resultant particles is mainly dependent on the orifice diameter. Produced beads usually have a size of more than 2 mm.

Electrostatic dripping is the acceleration of the normal droplet formation process using electrostatic forces to pull the droplets off the orifice at a considerably faster rate compared to the simple dripping process, whereby removal is based solely on gravitational force. An electrical potential is applied to the extruded whey protein solution by passing it through a charged nozzle, with the produced droplets subsequently falling into the iron-based curing solution, which has been earthed or holds an opposite charge. This technique is capable of producing smaller microbeads compared to normal dripping (≥50 microns in diameter), of uniform size and shape and is reproducible.

The coaxial air-flow technique like the electrostatic extrusion method, is based on the acceleration of the normal dripping process at an orifice, and uses a stream of compressed air to pull the whey protein droplets from the nozzle at a faster rate compared to the normal gravitational force. The coaxial concentric nozzle consists of an inner orifice, in which the whey protein solution is extruded and an outer orifice, through which the compressed air flows and strips the droplets formed at the tip of the internal nozzle. The process produces whey protein beads with diameters >200 microns, of uniform size and shape.

The production of whey protein iron beads by vibrating nozzle technique is based on the principle of controlled breakup of the laminar jet by the application of a controlled vibrational frequency with defined amplitude to the extruded whey protein liquid. Formation of microbeads using this method typically involves use of an encapsulator. See FIG. 1. Suitably, the iron encapsulator consists of a single orifice for transition of the extruded calcium depleted denatured whey protein. When the calcium depleted denatured whey protein liquid is extruded through a nozzle, the exerted frequency causes the continuous liquid stream to break up freely into uniform droplets of equal size which are subsequently hardened by landing in a curing solution. The sinusoidal force can be applied by either vibrating the nozzle (vibrating nozzle technique), pulsating the polymer in a chamber before passing through the nozzle (vibrating chamber technique), or periodic changes of the nozzle/orifice diameter during extrusion. This technique can produce whey protein iron beads of less than 150 microns in size.

Figure 16:
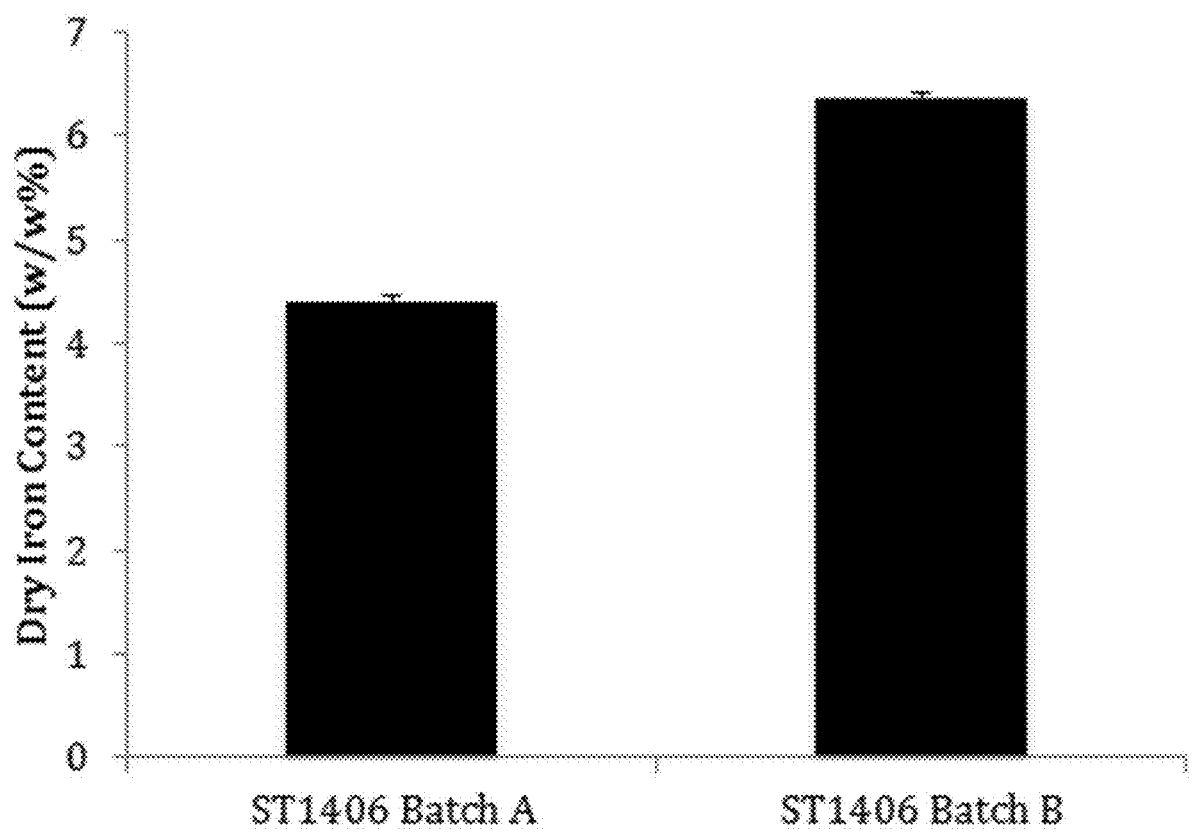
FIG. 16 shows the influence of electrostatic charge on iron loading in ST1406 microbeads of the invention (p<0.01 for difference). The increased iron loading while retaining the gastro-protective effects of the microbeads is advantageous because of cost, efficiency and practicality of dosing.

The vibrating technique can be used in combination with an electrostatic charge to produce droplets less than 100 microns in diameter. During droplet formation a net negative charge can be induced on the surface of the droplets using an electrostatic voltage system. The voltage system applies an electrostatic potential between the nozzle and an electrode placed beneath the nozzle. As the droplets fall through the electrode the induced charge causes them to repel one another and prevent coalescence, resulting in smaller droplets being formed compared to the standard procedure. Microbead size can be varied within a certain range by regulating the frequency of vibration and/or the flow rate of the polymer with higher frequencies and lower jet velocities enabling the generation of smaller microbeads of entrapped ferrous iron. Surprisingly, application of an electrostatic potential between the nozzle and an electrode placed beneath the nozzle also results in significantly higher iron content in the final microbeads of the invention (FIG. 16). Nonetheless, the main factor governing microbead size is the nozzle diameter, whereby the final microbead diameter is approximately 1.00-1.25× the size of the chosen nozzle when dried.

A combination of co-axial and vibrating nozzle technqiues can be used with or without the electrostatic charge to produce whey protein iron particles with a size of less than 50 microns. The whey protein solution is vibrated just before before passing through the co-axial nozzle and the resultant action of the two forces enables droples of less than 50 microns to be formed. Due to the small size of the particles and the turbulent conditions (formed by the air flow) coalsecences of the droplets can form and increase their size substantially above 50 microns. The elctroctstaic charge system as already mentioned causes inhibits coalescence. The use of the electroctatic charge system enales higher vibration frequencies and air flows to be used for a given nozzle size, enabling smaller whey protein iron beads to be produced.

A further technique for making microbeads of the invention is the jet cutting technique is based on the mechanical impact of a cutting wire on a liquid jet of calcium depleted denatured whey protein formed after extrusion through a nozzle. When the whey protein solution is forced through the nozzle at high velocity, a solid liquid jet is formed within a very short distance of the orifice. This jet can then be broken-up into equal cylindrical segments when passed through a cutting tool, which consists of several wires fixed onto a holder. Due to surface tension, these cylindrical segments form spherical droplets when passing through the air and are hardened after landing in a curing solution. The diameter of the resulting droplet is dependent on: (1) the number of cutting wires; (2) the number of rotations of the cutting tool; (3) the mass flow rate through the nozzle and (4) the mass flow depending both on the nozzle diameter and the velocity of the fluid. This method enables the production of small mono-dispersed homogenous shaped whey protein beads, >200 microns to several millimeters in diameter, with a narrow standard size deviation using viscous fluids at high production rates.

A further technique is the spinning disk atomization is a technique which is based on the disintegrating of a feed liquid of calcium depleted denatured whey protein which is performed on disc(s) to produce droplets. When the whey protein solution is dropped onto the surface of a rotating disk it is centrifugally accelerated to a high velocity which distributes it as a thin film on the disc. Depending on the flow rate of the feed, droplets are then released due to the centrifugal forces at the tip (teeth) of the rotating disk or from ligamentry streams released from the edge of the disk. The droplets are then gelled by landing in a curing solution which is position to collect the projectile droplets. The size of the droplets produced is determined mainly by the rotation speed of the disk. This technique can produce produce calcium depleted, denatured whey protein microbeads ≥200 µm in diameter with a narrow size distribution.

In the mechanical production procedures described above whey protein solutions are extruded through a single orifice (nozzle) system (excluding co-axial system) to produce calcium depleted denatured whey protein droplets which are hardened in curing solution consisting of iron. Additionally the whey-iron particle can be produced using a co-extrusion technique which uses a double (concentric) nozzle system. The concentric nozzle consists of an internal nozzle, in which the iron solution is extruded through, and is placed within an external nozzle which the whey protein solution passes through. The liquids meet at the tip of each nozzle to form a co-extruded solution containing iron in the whey protein solution. This co-extruded liquid can then be produced into droplets using as appropriate mechanical procedure (excluding co-axial system) as described above, resulting in the formation of a microbead containing a defined core comprising of iron in a denatured whey protein matrix. The size of the core and membrane can be varied by the varying the size ration of the internal and external nozzle and using this system whey protein iron beads of less than 200 microns can be formed.

Spray-drying is a unit operation in which a liquid polymer is firstly atomized by a compressed air stream and subsequently dried by a separate hot gas current in a drying chamber, allowing the formation of the particles. A 2-fluid nozzle is used in which air passes through an outside channel and atomizes the liquid stream passing through the inner channel. The liquid stream consists of a calcium depleted denatured whey protein and iron solution and is atomized into fine particles at the nozzle which are immediately dried by flash evaporation into whey protein beads entrapping the iron. The produced particles are collected using cyclone technology. This technique produces whey protein iron particles of between 10-50 microns. The dried particles can be further treated in additional curing solutions if required.

Two other techniques, which are known to persons versed in the art are three fluid nozzle techniques used in conjunction with a spray dryer and microfluidic devices.

One aspect of an embodiment of the invention comprises a composition comprising an amorphous preparation of iron salt associated with a protein-based carrier. The iron in the composition may comprise some ferric ($Fe^{3+}$) iron. This may be advantageous because ferric iron, when delivered to the GI tract, may give rise to a reduced level of gastrointestinal discomfort compared to ferrous iron. Ferric iron is cabaple of undergoing reduction in the intestine to ferrous iron, the substrate for DMT1 activity. However, the amorphous preparation of iron salt associated with a protein-based carrier typically has at least 50% ferrous ($Fe^{2+}$) iron which facilitates adequate bioavailability via absorption mediated by intestinal enterocyte DMT-1. Furthermore, the ferrous iron release from the composition of the invention at low pH and in the presence of the components of gastric fluid such as pepsin, is limited in order to protect the stomach and limit nausea, vomiting and epigastric pain.

In one aspect of an embodiment of the invention, the composition may be formed by mixing an iron-containing composition with a protein-based composition, and by drying the resulting mixture. In another aspect, where the mixture comprises ferrous iron, the drying step may result in converting at least a portion of the ferrous iron in the mixture to an amorphous preparation of iron salt in the ferric form associated with a protein-based carrier. The drying process might make use of additional materials such as Silicon Dioxide to prevent "caking" of the composition during drying.

This dried composition may be advantageous over non-dry compositions (including gel preparations), which can be more variable and/or less stable on storage, especially with respect to oxidation, and inconsistent in their production, collectively presenting challenges for formulation, scale up and dose optimisation. Beads not subjected to heating/drying present additional formulation challenges due to their bulk. Furthermore, undried composition of iron present technical and cost challenges from a compatibility perspective if it is desired to incorporate iron into a multi-active supplement, for example a multivitamin and/or multi-mineral supplement.

In some embodiments, conversion of ferrous (2+) iron into ferric (3+) iron during production of the composition may be brought about during drying. In other embodiments, the conversion of ferrous (2+) iron into ferric (3+) iron can be limited during drying by anti-oxidative effects of the whey protein, drying in an inert (e.g. nitrogen) atmosphere, and/or by incorporation of a stabilizer with anti-oxidative effects. This can include, but is not limited to, the following in whole or in part: beta-carotene and carotenoids; vitamin c; vitamin e; zinc; selenium; copper; manganese; astaxanthin; black pepper extract; co-enzyme Q10; lycopene; lysine based antioxidants, methylcobalamine; grape seed extract; lutein; ginseng; citrus bioflavonoids, orange peel extracts, green tea extract, ginko bilboa, spruline, wheat grass, barley grass, alfalfa, flax seed, banana leaf extract.

One embodiment of the invention is a method for making a composition comprising the steps of: preparing an iron-containing composition; preparing a protein-based composition (preferably denatured, calcium depleted whey protein/beta-lactaglobulin); mixing said ferrous iron containing composition with said protein-based composition; and converting at least a portion of the iron content of the mixture into an amorphous preparation of iron salt associated with a protein-based carrier. The iron-containing composition may comprise ferrous iron. At least a portion of the iron content of the mixture may be converted into a largely amorphous preparation of ferric iron associated with a protein-based carrier.

In another embodiment the method may be further specified such that: the ferrous iron-containing composition is a solution; the protein-based composition is a suspension of protein-based material; and the mixing comprises extruding the suspension through a vibrating nozzle such that the suspension is extruded in the form of microdroplets, the microdroplets being extruded into a bath comprising the solution such that beads are produced, the composition comprising said beads.

In some embodiments the conversion is achieved during drying of the composition. If the drying process is carried out in air or in the presence of oxygen, it is believed that this drying process has the effect of oxidising at least a portion of the iron content such that it changes from a predominantly ferrous (2+) state to an amorphous preparation of iron salt associated with a protein-based carrier where a proportion of the iron is in a ferric (3+) state.

In another embodiment, a divalent metal ion is substituted for iron in a composition described herein. Such metal ions include zinc, manganese, copper, chromium, selenium, molybdenum, combinations thereof, or combinations thereof with iron. In certain embodiments the resulting beads have improved palatability (e.g. Iron sulfate, zinc sulfate).

Experimental

Generation of Microbeads (a) De-Calcification of Whey Protein

WPI was treated with ion exchange resins to replace divalent (e.g. calcium) cations with monovalent cations.

(b1) Encapsulation of Ferrous Iron—Example 1 (ST1406)

Calcium-depleted WPI was used for ferrous encapsulation following particle formation using the mechanical based techniques described above. The ferrous iron encapsulation system was prepared using the calcium-depleted WPI, which contains (per 100 g) more than 1 g elemental iron and up to 95 gram protein. Microbeads composed of a ferrous sulfate whey protein gel matrix were prepared using the extrusion jet-breakup technique. A stock solution of whey protein was prepared in phosphate buffer (pH 7; 2M) in a blade mixer or Ultra-Turrax in the presence of a surfactant in the range of 0.01-0.1% (w/w) at pH range 6.0-7.0. The solution is filtered through a 150 micron filter. Whey protein isolate (WPI) was subsequently heat-denatured at appropriate environmental conditions (pH 7.0, >78° C.; 4-11% w/w protein content). Heat treatment was performed between 70-140° C. at pH in the range of 5.0-8.5. Heat denaturation was performed under agitation (150-200 rpm) to enable the production of a soluble suspension of protein aggregates. Heat denaturation was performed for a between 30 and 90 minutes to allow denaturation and exposure of hydrophobic sites.

After Protein Activation (i.e. heat denaturation), the solution of aggregates was rapidly cooled to room temperature and then held overnight at 4° C. with constant agitation.

The resulting whey protein oligomer solution was extruded through a multinozzle plate into a curing solution maintained at 60-65° C., with a total molality of 5M), at pH 3.8, containing ferrous sulfate 0.5M and Tween 20 at 0.035% (m/m). Spherical microbeads were obtained by the application of a vibrational frequency with defined amplitude to the co-extruded jet and collected in the curing solution placed 18 cm below the nozzle and agitated by a magnetic stirrer (length 4 cm) in dish with diameter 35 cm. Polymer flow rate and vibrational frequency were empirically determined for the specific viscosity and concentration of calcium depleted denatured whey protein. Gel microbeads were agitated (50 rpm) for a minimum of 30 min. These microbeads were then recovered and washed with ultrapure, sterile water or first dispersed in tri-sodium citrate or sodium ascorbate (up to 0.5M) for 15 minutes and subsequently washed with sterile water.

(b2) Encapsulation of Ferrous Iron—Example 2

The microbeads of the invention can be manufactured by co-extruding the calcium depleted oligomeric whey protein solution through a concentric nozzle system into a curing solution containing sodium ions at 0.5 M with a pH adjusted to the range 3.2-4.0 through the addition of acetic acid. Spherical microbeads were obtained by the application of a vibrational frequency with defined amplitude to the co-extruded jet and collected. The appearance of a protein-iron gelation upon contact with acetate curing solution, occurred at a minimal calcium depleted denatured protein concentration of 2.5% (9% diluted to 2.5%). For the purpose of optimum ferrous encapsulation using a concentric nozzle system, the protein concentration must be greater than 5.5% (w/w) whey protein at pH greater than 5.1. Microbeads were recovered and dispersed in a second acidic solution (e.g. tri-sodium citrate 0.25M) and subsequently washed with ultrapure water.

(b3) Scale Up Encapsulation of Ferrous Iron—Example 3

While producing iron containing whey protein hydrogel beads could produce useful beads at small scale, the conditions were not suitable for large scale production. Some of the issues include the high acetic acid content of the curing solution which contributes to spontaneous gelling in the extrusion nozzle, the droplet deformation of the low density protein solution when entering into the high density curing solution and the coalescence of the partially gelled protein beads on the surface of the curing solution. To overcome these difficulties the composition and properties of the curing solution as well as the protein solution was studied in detail and improved. Total elimination of the buffering system relying exclusively on iron(II) and sulfate electrolytes for gelling was found to be unsuitable.

The most influential factors that governed the density, surface tension and the speed of gelation of the curing solutions and the results were interpreted through statistical analysis of the combinations of conditions described below.

group and a sulfonic or carboxyl group include betaines or sulfobetaines and natural substances such as aminoacids and phospholipids (phosphatidylcholine, sphosphatidylethanolamine). Anionic surfactants can be sulfates, sulfonates, phosphate esters and carboxylates, for example, but not exclusively sodium lauryl sulfate (SDS).

Protein concentrations between 10.5-11.5 w/w % were prepared. Preferably the protein solution had a concentration 10.5% otherwise spontaneous gelling occurred occasionally. The protein was denatured by either conductive or radiation (microwave) heating at a temperature between 60-100° C., ideally 80° C., for a time period of 30 min-120 min, ideally 45 min. The denatured protein solution was used immediately or could be aged at 4-8 C for 1-24 h, ideally 12 h.

The molality of the curing solution was 0.35 mol/kg water while the low settings of the iron content was 0.125 mol/kg water. Tween 20 or SDS was used at its CMC level. 0.125 mol/kg iron content generated bead droplets that sank rapidly and allowed a large surface area for faster gelling to occur.

In this approach to curing the extruded calcium depleted denatured whey protein solution, the sodium acetate-acetic acid buffer and a freshly prepared iron(II) sulfate heptahydrate solution were mixed in 1:1 solvent ratio. Tween 20 was

|  | Molality (mol/kg solvent) | pH | $OAc^-$ (mol/kg) | $SO_4^{2-}$ (mol/kg) | $Cl^-$ (mol/kg) | $H^+$ (mol/kg) | $Na^+$ (mol/kg) | $Fe^{2+}$ (mol/kg) | Ionic strength ($\mu$) |
|---|---|---|---|---|---|---|---|---|---|
| Buffer I. | 3 | 3.5 | 0.152 | 0.500 | 0.000 | 0.000 | 0.152 | 0.500 | 2.17 |
| Buffer I. | 0.7 | 3.5 | 0.036 | 0.500 | 0.000 | 0.000 | 0.036 | 0.500 | 2.06 |
| Buffer I. | 3 | 4.0 | 0.324 | 0.500 | 0.000 | 0.000 | 0.324 | 0.500 | 2.34 |
| Buffer I. | 0.7 | 4.0 | 0.076 | 0.500 | 0.000 | 0.000 | 0.076 | 0.500 | 2.10 |
| Buffer I. | 3 | 3.5 | 0.152 | 0.250 | 0.000 | 0.000 | 0.152 | 0.250 | 1.17 |
| Buffer I. | 0.7 | 3.5 | 0.036 | 0.250 | 0.000 | 0.000 | 0.036 | 0.250 | 1.06 |
| Buffer I. | 3 | 4.0 | 0.324 | 0.250 | 0.000 | 0.000 | 0.324 | 0.250 | 1.34 |
| Buffer I. | 0.7 | 4.0 | 0.076 | 0.250 | 0.000 | 0.000 | 0.076 | 0.250 | 1.10 |
| Buffer II. | 3 | 3.5 | 0.152 | 1.174 | 0.000 | 0.000 | 1.500 | 0.500 | 4.19 |
| Buffer II. | 0.7 | 3.5 | 0.036 | 0.657 | 0.000 | 0.000 | 0.350 | 0.500 | 2.53 |
| Buffer II. | 3 | 4.0 | 0.324 | 1.088 | 0.000 | 0.000 | 1.500 | 0.500 | 4.11 |
| Buffer II. | 0.7 | 4.0 | 0.076 | 0.637 | 0.000 | 0.000 | 0.350 | 0.500 | 2.51 |
| Buffer II. | 3 | 3.5 | 0.152 | 0.924 | 0.000 | 0.000 | 1.500 | 0.250 | 3.19 |
| Buffer II. | 0.7 | 3.5 | 0.036 | 0.407 | 0.000 | 0.000 | 0.350 | 0.250 | 1.53 |
| Buffer II. | 3 | 4.0 | 0.324 | 0.838 | 0.000 | 0.000 | 1.500 | 0.250 | 3.11 |
| Buffer II. | 0.7 | 4.0 | 0.076 | 0.387 | 0.000 | 0.000 | 0.350 | 0.250 | 1.51 |
| Buffer III. | 3 | 3.5 | 0.152 | 0.500 | 1.348 | 0.000 | 1.500 | 0.500 | 3.52 |
| Buffer III. | 0.7 | 3.5 | 0.036 | 0.500 | 0.314 | 0.000 | 0.350 | 0.500 | 2.37 |
| Buffer III. | 3 | 4.0 | 0.324 | 0.500 | 1.176 | 0.000 | 1.500 | 0.500 | 3.52 |
| Buffer III. | 0.7 | 4.0 | 0.076 | 0.500 | 0.274 | 0.000 | 0.350 | 0.500 | 2.37 |
| Buffer III. | 3 | 3.5 | 0.152 | 0.250 | 1.348 | 0.000 | 1.500 | 0.250 | 2.52 |
| Buffer III. | 0.7 | 3.5 | 0.036 | 0.250 | 0.314 | 0.000 | 0.350 | 0.250 | 1.37 |
| Buffer III. | 3 | 4.0 | 0.324 | 0.250 | 1.176 | 0.000 | 1.500 | 0.250 | 2.52 |
| Buffer III. | 0.7 | 4.0 | 0.076 | 0.250 | 0.274 | 0.000 | 0.350 | 0.250 | 1.37 |

The main factors that were found to influence the density were iron(II) sulfate and buffer concentration and the curing solution temperature. The surface tension modified by the surfactants (SDS, Tween 20, Tween 80) and the buffer concentration. Different surfactants have different effects on the curing solution. All of the selected surfactants seemed to have a great influence on the surface tension but the effect of anionic surfactants was found to be superior. Unexpectedly, the anionic surfactant significantly decreased the density of the curing solution. This is advantageous because it increases the rate of immersion of the solidifying microbead and promotes curing.

Non-ionic surfactant include polyoxyethylenes, poloxamer, poloxamine or polysorbates, for example, but not exclusively Tween 20 or Tween 80. Zwitterionic surfactants, where the polar head group consists of a quaternary amine also added. The molality of the curing solution acetate buffer ranged from 0.7 to 6.44 mol/kg water before mixing, giving a rise to 0.35 to 3.22 mol/kg water when calculated for the curing solution. The molality of the prepared iron(II) sulfate heptahydrate solution was in the range of 0.25-2.0 mol/kg water, giving a rise to 0.125-1.0 mol/kg water when calculated for the curing solution. The concentration of the surfactant was in the range of 1-5 times its critical micelle formation concentration (CMC) value. The pH of the curing solution, right before the beginning of the extrusion process was in the range of 3.2-4.2 and preferably 3.5-3.6. The temperature of the curing solution during the extrusion process was in the range of 20-65° C., preferably 40° C.

Characterisation of Microbeads

X-Ray Diffraction

PXRD measurements were performed on samples placed on a low background silicon sample holder, using a Rigaku Miniflex II desktop X-ray diffractometer (Rigaku, Tokyo, Japan). The PXRD patterns were recorded from 5° to 80° on the 2θ scale at a step of 0.05°/s. Xray tube composed of Cu anode ($\lambda$CuK$\alpha$01.54 Å) was operated under a voltage of 30 kV and current of 15 mA.

Thermogravimetric Analysis

Thermogravimetric analysis (TGA) experiments were conducted on a Pyris 1 Thermogravimetric Analyser (Perkin Elmer). Weighed, powdered samples (10-15 mg) were analysed in open ceramic pans. All samples were measured under the following temperature program: isothermal at 30° C. for 5 min; gradient from 30° C. to 100° C.; isothermal at 100° C. for 20 min; gradient from 100° C. to 900° C. at 10° C./min rate and under air purge. Sample water content is calculated from the weight difference at the end of the 100° C. isotherm and the initial sample weight.

Scanning Electron Microscopy

The scanning electron microscopy (SEM) images were recorded on a Zeiss Ultra Plus Field Emission SEM with a Gemini® column (Zeiss). The dry sample beads were placed on a conducting carbon tape without any further preparation or sample coating. Accelerating voltages between 2-3 kV was used to overcome the extensive discharge effect.

In Vitro Dissolution

Measurement of Iron II

A solution of iron (II) sulfate in water (10 mM) was serially diluted using pH 1.8 KCl buffer. Aliquots (100 μl) of the diluted solutions were added to a 96-well plate containing 100 μl of 1,10-phenanthroline (5 mM). The plate was read at 490 nm on a multiwall plate reader in order to construct a calibration curve. Dissolution samples were diluted ten-fold typically at pH 1.6 into phenanthroline (5 mM) and the samples read rapidly under $N_2$ blanketing.

Measurement of Iron III

A 50 mg quantity of beads was transferred to a vial containing 10M HCl (10 ml) and left overnight at room temperature. The resulting solution was shaken and then a 100 μl aliquot was transferred into 900 μl of 10M HCl. A 100 μl aliquot of the diluted solution was added to a 96-well plate containing 1M sodium thiocyanate (100 μl). Absorbance was measured at 450 nm on a multiwell plate reader. The concentration of the iron III was estimated by reference to a series of iron III standard solutions.

Simulated Intestinal Dissolution Method

An accurately weighed sample (approximately 50 mg) of microbeads was transferred into a three necked vessel into which had been placed 15 ml pH 6.6 buffers (containing 0.1 M sodium bicarbonate, 10 mg/ml bile acid extract, 1.85 mg/ml pancreatin, adjust to pH 6.6 with 1M HCl) at 37° C. Generally, at 1, 15, 30, 45, 60 and occasionally at 90, 120 min time points, samples were taken for iron (II) and iron (III) measurement. For iron II measurement, 100 μl of the dissolution supernatant was diluted into 900 μl pH1.8 buffer. For iron III measurement, a 100 μl aliquot of the dissolution supernatant was diluted to 900 μl in 10M HCl and left overnight at room temperature. After the final time point, all the buffer solutions were taken out and 10 ml 10M HCl was added to the flask and left overnight. The beads were fully dissolved overnight and 100 μl solution was added to 900 μl 10M HCl for total iron III level measurement.

Simulated Gastric Acid Dissolution Method

An accurately weighed sample (approximately 50 mg) of microbeads was transferred into 15 ml of pH 1.6 buffer containing NaCl (34.2 mM), sodium taurocholate (80 μM), 0.1 mg/ml pepsin, and adjusted to pH 1.6 with 1M HCl at 37° C. Samples were typically taken for Iron (II) and Iron (III) measurement at 1, 15, 30, 45, 60, 90, 120 min. For iron II measurement, 100 μl of the solution was removed and diluted into 900 μl pH 1.8 buffer. For iron III measurement, 100 μl of the solution was diluted to 900 μl in 10M HCl and left overnight at room temperature. After the 2 h time point, all the buffer solutions were taken out and 10 ml 10M HCl was added to the flask and left overnight. The microbeads were fully dissolved after overnight. A 100 μl aliquot was added to 900 μl 10M HCl for total iron measurement and indirect estimation of residual iron after 120 min dissolution.

The iron II and iron III dissolution methods were validated for accuracy and precision.

Measurement of Iron II in the Microbeads

A sample of microbeads was crushed in a mortar and pestle or milled in a ball mill. A 1 g sample was transferred to a glass vial equipped with a magnetic stirrer, to which was added 10 mL dilute aqeuous HCl (0.1 M) which had been nitrogen sparged to remove oxygen. The suspension was heated to 50° C. and then subjected to ultrasonication until the crushed beads dissolved. A 0.1 mL aliquot was removed under nitrogen and rapidly transferred for measurement of iron II using the phenanthroline method described above.

Palatability Data

Subjects (n=6) were randomly allocated to aqueous dispersions of microbeads of the invention (ST1406) in apple juice (100 mL) in comparison with equimolar doses of ferrous sulfate in acidified water and apple juice (100 mL) and asked to rate the formulations for:

- overall taste on a Likert scale of 1-5 (Where 1 represents extremely unpleasant and 5 represents extremely pleasant);
- after-taste on a Likert scale of 1-5 (Where 1 represents extremely unpleasant after taste in your mouth and 5 represents extremely pleasant taste. 3 represents no noticeable taste);
- compliance and how satisfied they would be to take this supplement on a daily basis on a Likert scale of 1-5 (Where 1 represents extremely unhappy and 5 represents extremely happy. 3 represents indifferent);
- texture/mouth feel on a Likert scale of 1-5 (Where 1 represents extremely unpleasant texture or feel in the mouth and 5 represents extremely pleasant texture/mouth feel. 3 represents neither pleasant nor unpleasant texture or mouth feel);

The results show that the beads score highly on taste, after taste and compliance measures, all significantly greater (p<0.02) than ferrous sulfate in acidified water. On texture, the two formulations are quite different, the invention being solid beads and FeSO4 being a solution. Despite this there was no preference of either formulation on average. Accordingly, beads prepared in accordance with the invention are significantly more palatable than FeSO4 in aqueous solution. The results of this study are presented in FIG. 2.

In-Vivo Tolerability Data

Three subjects from the taste test had a history of intolerance to ferrous iron preparations, even at low doses, and suffered upper gastrointesinal symptoms during the taste test. In a separate study using random, blinded, prospective allocation to beads prepared in accordance with the invention or FeSO4.7H$_2$O in identical size 0 gelatin capsules, in-vivo gastrointesinal tolerability was assessed in a crossover design. The test articles were taken in the morning after fasting for 10 hours with baseline and 2 hour fasting blood draws. After 2 hours fasting, food was taken as normal and over the following 24 hours, a modified Gastrointestinal Symptom Rating Scale (GSRS) was completed. This rates the following symptoms as 0=none, 1=mild, 2=moderate, 3=severe:

Abdominal pain/cramps
Nausea/vomiting
Abdominal bloating
Borborygmus (abdominal rumbling)
Flatulence/wind In addition the products were taken on 3 consecutive days and the Bristol Stool Chart was used to assess constipation/diarrhoea. Positive score changes from baseline normality (=0) indicated constipation.

The results show that in the setting of established gastrointestinal intolerance to ferrous sulfate, beads prepared in accordance with the invention are well tolerated. Significantly higher symptoms scores were observed for abdominal pain/cramps, nausea, flatulence (all p=0.02) and constipation (p=0.03). Beads prepared in accordance with the invention are significantly better tolerated from a gastointestinal point of view than FeSO4 (see FIG. 3).

In-Vivo Efficacy Data

We evaluated the formulation in a randomised, double-blind, controlled with a 28 day cross-over to obtain a minimum of 6 paired evaluable healthy subjects with serum ferritin <100 ng/mL for comparison of the invention versus FeSO4.

To be considered eligible for enrolment into the study, subjects were required to:
1. Be able to give written informed consent;
2. Be between 18 and 40 years of age;
3. Be a non-pregnant female;
4. Be in generally good health as determined by the investigator.

Subjects were excluded from the study if they were:
1. Less than 18 and greater than 65 years of age;
2. Pregnant females, lactating or wish to become pregnant during the study. [Included female subjects were either of non-childbearing potential (i.e., physiologically incapable of becoming pregnant, including any female who is post-menopausal or any female who is surgically sterilized (via documented hysterectomy or bilateral tubal ligation), OR were of childbearing potential, and not lactating and had a negative urine pregnancy test at the screening visit, visit 2 and upon completion of the study at visit 7. In addition, the subject if female and of childbearing potential also agreed to one of the following methods of contraception:
   i. Complete abstinence from intercourse two weeks prior to administration of study drug, throughout the clinical trial, until the completion of follow-up procedures or for two weeks following discontinuation of the study medication in cases where subject discontinues the study prematurely. (Subjects utilizing this method must agree to use an alternate method of contraception if they should become sexually active and will be queried on whether they have been abstinent in the preceding 2 weeks when they present to the clinic for the Final Visit.) or,
   ii. has a male sexual partner who is surgically sterilized prior to the Screen Visit and is the only male sexual partner for that subject or,
   iii. sexual partner(s) is/are exclusively female or,
   iv. Oral contraceptives (either combined or progestogen only) with double-barrier method of contraception consisting of spermicide with either condom or diaphragm. (Women of child-bearing potential using an oral contraceptive in combination with a double-barrier method of contraception are required to continue to use this form of contraception for 1 week following discontinuation of study medication).
   v. Use of double-barrier contraception, specifically, a spermicide plus a mechanical barrier (e.g. male condom, female diaphragm). The subject must be using this method for at least 1 week following the end of the study or,
   vi. Use of any intrauterine device (IUD) with published data showing that the highest expected failure rate is less than 1% per year. The subject must have the device inserted at least 2 weeks prior to the first Screen Visit, throughout the study, and 2 weeks following the end of the study.];
3. Hypersensitive to any of the components of the test product;
4. Suffered from a metabolic disorder;
5. Had any evidence of current infection (viral, bacterial, other);
6. Were taking any iron supplements;
7. Had a significant acute or chronic coexisting illness (cardiovascular, gastrointestinal, endocrinological, immunological, metabolic or any condition which contraindicates, in the investigators judgement, entry to the study);
8. Had a condition or taking a medication that the investigator believes would interfere with the objectives of the study, pose a safety risk or confound the interpretation of the study results;
9. Consumed more than the recommended alcohol guidelines i.e. >21 alcohol units/week for males and >14 units/week for females;
10. Had a history of illicit drug use;
11. Were, in the opinion of the investigator, considered to be poor attendees or unlikely for any reason to be able to comply with the trial;
12. Subjects may not be receiving treatment involving experimental drugs. If the subject has been in a recent experimental trial, these must have been completed not less than 30 days prior to this study;
13. Had a malignant disease or any concomitant end-stage organ disease;

The study was conducted in accordance with the ICH Guidelines on Good Clinical Practice, and the declaration of Helsinki.

From a screening cohort of up to 20 people, it was estimated that up to 12 healthy subjects would be eligible for randomization and would result in 10 evaluable subjects subject to exclusion criteria. Based on previous clinical data using serum iron measurements in fasting subjects with normal haemoglobin and ferritin levels below 100 ng/mL over 6 hours, it was expected that the Trough To Peak Differential (TPD) of beads prepared in accordance with the invention would be at least 50% greater than FeSO4 in paired analyses. The expected mean±standard deviation of TPD for beads prepared in accordance with the invention will be 20.0±3.0 micromol/L. With 85% power and a two-sided alpha of 0.05, we required 6 subjects per group. Because this is a pilot study with a 10% expected drop out, we screened 20 subjects and aimed to include n=12 subjects per group in the cross-over study. A minimum of 6-paired evaluable subjects was required.

Subjects underwent an initial phone screen and were asked questions regarding their eligibility for the study. Eligible subjects were scheduled for a screening visit. Study participation involved 3 study visits over a period of 4-6 weeks.

At the first visit (Visit 1) the overall details of the study were explained and informed consent was obtained. Vitals, body weight and Body Mass Index (BMI) were recorded and medical history and general health was recorded. An Irritable Bowel Questionnaire was administered to determine whether subjects were at risk of any pre-existing chronic inflammatory bowel conditions. For women of childbearing age a urine sample was collected and pregnancy test performed.

During Visit 1, the subject's eligibility was determined by reviewing the inclusion and exclusion criteria (see above). A fasting venous blood sample (8 ml) was collected and a full blood count was performed to evaluate potential for intercurrent infection, along with serum iron, transferrin saturation and ferritin. Subjects were between 18 and 65 years of age.

The visit windows are set as outlined in the table and text below:

|  | Day | | |
| --- | --- | --- | --- |
|  | Screening | Day 1 Visit | Day 28 |
|  | 1 | 2 | 3 |
| Informed Consent | X | | |
| Inclusion/Exclusion | X | | |
| Vitals | X | | |
| Demographic Data | X | | |
| Fasting Blood Sample (8 ml) | X | | |
| Urine Pregnancy Test (if applicable) | X | | |
| Randomization | | X | |
| Study Product Administered | | X | X |
| Blood Sampling (20 mls) | | X | X |
| Adverse Events recorded | | X | X |
| Concomitant Medications Record | | X | X |

In the analyses, comparisons between groups were conducted using paired sample t-tests for continuous variables and Wilcoxon's Rank Order tests for non-normal distributions. Shapiro-Wilks tests for normality were used to confirm assumptions that primary and secondary endpoints in the study population come from a normal distribution. If assumptions of normality were not possible, log-transformation was used or Wilcoxon's Rank Order tests were applied.

All analyses were two-sided, and significance set at $\alpha=0.05$. Chi-squared analyses, was used to compare categorical variables. Data were presented as the mean value ± the standard error of the mean for continuous variables unless otherwise stated while frequencies and percentages were used for categorical variables. All analyses were carried out using SPSS V.11 statistical software (Statistical Package for the Social Sciences: SPSS Inc, Chicago, Ill., 2001).

Study Visits
Screening Visit (Up to Day −28/Visit 1)

From the screening visit, two males and eight females were selected to continue in the study, based on their serum iron and ferritin levels. A fasting blood sample (8 mls) was collected at the screening visit, and a full blood count (FBC), serum iron, unbound iron binding capacity, derived total iron binding capacity and transferrin saturation were calculated. Ferritin and haemoglobin were also assessed. A white cell count was used to confirm absence of intercurrent infection.

Visit 2 (Baseline/Day 0)

Subjects returned to the study site (within two weeks of Visit 1) for the first intervention day (Visit 2), after fasting since 10 pm the previous night. Subjects were pre-randomised into one of the two treatment groups with a washout period of four weeks between treatment phases:
 Group 1: beads prepared in accordance with the invention, followed by FeSO4
 Group 2: FeSO4, followed by beads prepared in accordance with the invention A blood sample was collected immediately after drinking the supplement and at 2 hours, 4 hours and 6 hours after dosing. A full blood count (FBC) was carried out as well as serum iron, unbound iron binding capacity, derived total iron binding capacity and transferrin saturation. Ferritin and haemoglobin were also assessed. A white cell count was again used to confirm absence of intercurrent infection. At follow up timepoints, 4 mLs blood was drawn and serum iron, unbound iron binding capacity, derived total iron binding capacity and transferrin saturation were reassessed. A total of 20 mls of blood was collected throughout the study day.

Water was consumed ad libitum, and after the 4-hour blood collection, a light snack with low iron content was given to the subjects. Subjects were observed during the duration of the study, were not allowed to leave the test centre and were not permitted to have any other foods or drinks because of the risk of interference with iron analysis. Subjects were queried about any changes in their health status. Any adverse events or serious adverse events were recorded.

Visit 3 (Baseline/Day 28)

Subjects returned to the study site after a four-week washout for the cross-over and during this period they were instructed to follow their standard diet and exercise routine and not consume medications, especially iron supplements, that could interfere with the assessment of the study product.

During the follow up visit (day 28), a full blood count (FBC) was carried out as well as serum iron, unbound iron binding capacity, derived total iron binding capacity and transferrin saturation was carried out at baseline, following an 10 hour overnight fast from food and tea/coffee. Ferritin and haemoglobin were also assessed. Once again, a white cell count was used to confirm absence of intercurrent infection.

Subjects were given a single dose of the alternative test supplement. At follow up timepoints, 4 mLs blood was drawn and serum iron, unbound iron binding capacity, derived total iron binding capacity and transferrin saturation were reassessed.

All samples were shipped directly to Biomnis for analysis. A total of 48 mls of blood was collected from each subject throughout the study.

Subjects were withdrawn from the study if the subject:
 Elects independently to withdraw from the study;
 If he/she develops any condition which contravenes the original criteria;
 Is considered at any point to be unsuitable to continue the study, at the discretion of the investigator.

Results

The primary endpoint in this study is serum iron Trough to Peak Differential (TPD) over 0-6 hours and shows superiority of ST1406 beads prepared in accordance with the invention over FeSO4. This is presented as mean (±SEM) increase in serum iron from baseline in FIG. 6 The median TPD for the beads was 20.1 µmol/L [IQR: 16.1-21.7] while the value for FeSO4 was 9.7 µmol/L [IQR: 7.4-13.6], p=0.017. FIG. 6 also presents the relative time course of mean (±SEM) serum iron profile over the study period for both test articles. Compared to FeSO4, there were significant differences between serum iron levels at timepoints 2 hours and 4 hours in the analysis of the beads (both p<0.05). The combined values within each group for the primary and secondary efficacy measures at time 1 and time 2 were found not to significantly deviate from normality (Shapiro-Wilks p values all >0.05).

For the secondary endpoints, the median AUC 0-6 hr (μmol/L·hr) for serum iron with beads was 83.7 [IQR 97.5-72.5] compared to 42.1 [IQR 62.5-31.0] p=0.025. The relative bioavailability of beads (n=8) was 199%±36% of FeSO4 over 0-6 hours, p=0.025. Similar results were found with transferrin saturation (TSAT) % and ST1406 microbeads showed significantly greater 2 hour TSAT % with beads compared with FeSO4 in paired analysis. The data demonstrate that beads outperform FeSO4 on all serum iron measures of efficacy. Consistent with preliminary clinical testing, there were no reports of adverse events with the beads.

EXAMPLE 3

Determination of Optimum Means of Mixing

In one embodiment of the invention, the maximum premix load of iron for mixing with 9% whey protein isolate was 10-15 mM ferrous sulfate. In some embodiments, pre-processing of the protein-based material, solution pH and the form of iron used had an effect on the product. For example, in some embodiments, adequate hydration of the protein-based material was required and ferrous sulfate heptahydrate was found to be preferable to dried ferrous sulfate because of the better water solubility and purity.

EXAMPLE 4

Preparation of the Protein-Based Solution

In one embodiment of the invention, whey protein isolate (WPI) was dispersed in 250 mL sterile water 10.5% w/v and left to hydrate for 2-16 hours at 4° C. under slight agitation (180 rpm). The pH of the dispersion was adjusted to 7 using HCl. The pH adjusted dispersion was optionally filtered through successive filters and then optionally finally through Durapore® 0.45 μm HVLP. The protein dispersion was then heated to 80 (75-90)° C. for 45-60 min under agitation (95 rpm). The dispersion was then cooled on ice and stored at 4° C. for 16 h.

EXAMPLE 5

Preparation of the Curing Solution

In some embodiments of the invention, the pH of the iron salt-containing curing solution (containing monovalent or divalent metal ions in the range 0.1 to 0.5 M) was adjusted to between pH 4.0 and 6.5. Ideally a pH of between 4.5 and 5.5 is used for the curing solution. Ferrous sulfate (0.1 to 1.0M) was added to the curing solution and pH further adjusted. The solution was then heated to 45° C. Optionally a low concentration surfactant was added. The solution was then maintained at 45° C.

EXAMPLE 6

Encapsulator Set Up

The following description is made with reference to FIG. 1. The falling distance for the curing solution was set to approximately 30 cm. The curing solution was stirred at 100 RPM. The 200 micron nozzle was attached to the vibrating nozzle apparatus. The following encapsulator set up applies to the Buchi/Inotech encapsulator, by way of example, but the person having skill in the art would appreciate how to implement analogous setups using other equipment. Set the vibrating nozzle to 1500 Hz, turn on the stroboscopic lamp, set the flow to 2-4 mL/min and adjust until a droplet chain is obtained, turn on the electrostatic dispersion unit with electrostatic tension of greater than 1.0 kV, an amplitude of 7.0 kV (4.7 to 7 kV), adjust the vibration (1000 to 2000) Hz to optimise bead formation, leave beads in the curing solution for 30 minutes. Bead particle size can be modulated by varying processing conditions such as the nozzle size, flow rate, vibration frequency.

EXAMPLE 7

Gel Bead Production

The pH of the curing solution is monitored and maintained at pH 3.2 to 4.0. After 30 minutes of curing, the beads are filtered and washed with water at room temperature. The beads are sampled (known weight) and the iron content of beads is confirmed per w/w gel bead for the batch using sodium thiocyanate method following dissolution in 10M HCl. A sample of the gel beads is used immediately for evaluation of release of ferrous iron or stored in an airtight container with N2 atmosphere to minimise oxidation of ferrous to ferric iron. Optionally, the beads can be prepared under N2 atmosphere or in the presence of anti-oxidants to preserve the iron form in a reduced state if ferrous starting material is used.

EXAMPLE 8

Production of Dry, Amorphous Preparations of Iron Associated with Protein

The gel beads are dried at 25° C. for 16 hours or at up to 80° C. for 2-16 hours to form dry, amorphous preparations of iron associated with protein beads. Thermogravimetric analysis is used to determine the water content of the amorphous iron. The beads are sampled (known weight) and iron content of beads confirmed per w/w dry bead for the batch using sodium thiocyanate method following dissolution in 10M HCl. The dry, amorphous iron-protein beads are sealed in an airtight container.

EXAMPLE 9

Bead Analysis

A standard sodium thiocyanate method was used to determine the total iron content of the protein beads and expressed as % w/w beads. Total iron was determined by treating approximately 100 mg beads with 100 ml of 10M HCl at 60° C. for two hours to fully dissolve the beads. Then solution was diluted to 10 times in 10M HCl. 100 μl of diluted solution was reacted with 100 μl 1M sodium thiocyanate. The concentration of the iron III ions was determined by measuring absorbance of the complex at 495 nm and comparing to the calibration curve. In addition to light microscopy, further image analysis was performed using a Leica TCS SP5 confocal scanning laser microscope (CSLM) for the purpose of micro-capsule morphology assessment. The mean size distribution and D (v, 0.9) (size at which the cumulative volume reaches 90% of the total volume) was evaluated using fifty beads per batch, which were analysed using a bright-field light microscope at a magnification maximum ×40.

The dissolution profile of the beads was studied by incubating the beads in pH 1.6, pH 6.6, and pH 8.4 buffers at 37° C. degrees. The iron II and iron III levels were measured at 0, 15, 30, 45, 60, 90, 120 minute time points. Iron II level was measured by taking 100 µl of the solution at each time points into 900 µl water, Iron II ion was determined by the standard complexometric titration with 5 mM 1,10 phenanthroline by measuring absorbance of the complex at 450 nm and comparing to the standard curve. Iron II measurement was carried out with appropriate suppression of artifactual oxidation to iron III by performing analysis under a nitrogen atmosphere. For iron III measurement, 100 µl of the solution was diluted to 900 µl 10 M HCl and left overnight at room temperature to oxide fully. Iron III content was determined using the standard sodium thiocyanate method described above.

An upper limit of approximately 9% betalactoglobulin—BLG—(11% denatured WPI equivalent to 9% BLG) was used to avoid spontaneous gellification of the BLG/WPI. Bead production was performed using a curing solution comprising up to 250-1000 mM sodium acetate along with up to 250-1000 mM ferrous sulfate, with curing for 30 minutes. The gel beads produced contained between 0.5 and 2% w/w iron and when dried using conditions ranging from 15° C. for 16 hours to 70° C. for 2 hours, the compositions had between 2.5% w/w iron and 10% w/w iron respectively.

The gel beads made were up to 8000 microns in diameter and the resulting dry, amorphous iron-protein beads had a diameter ranging from one third to one half the diameter of the gel beads. Three batches of beads made using 10.5% WPI solution cured with 250-1000 mM sodium acetate along with up to 250-1000 mM ferrous sulfate, with curing for 30 minutes were tested using different processing conditions allowing formation of a predominantly Fe3+ releasing bead or preserving the iron in the predominantly Fe2+ state. These had average particle diameters of between 1.84 mm±0.12 mm and 2.10 mm±0.16 mm (average 1840 and 2100 micron respectively). Further batches of micronized beads (100-300 micron) were made using microencapsulation technology and the results show improved absorption of iron with a compromise on processing characteristics such as flow and aggregation at low particle sizes, which can be improved by addition of silicon dioxide. The dry, amorphous iron-protein beads have better flow characteristics than gel beads, which makes them more amenable to formulation. Furthermore, the dry, amorphous iron-protein beads can be more easily formulated in regular capsules unlike gel beads. They can be co-formulated with vitamins and minerals without disruption of the bead structure or dissolution of the water-soluble vitamins which can promote instability of the vitamins and also loss of gel structure.

The dry, amorphous iron-protein microbeads produced are durable and stable. It has been shown that dry, amorphous iron-protein microbbeads left in ambient and accelerated stability storage conditions for several months show solid-state characterisation similar to the original beads and also perform as well as freshly made samples in terms of iron II release at pH 6.6.

When the dry, amorphous iron-protein beads are dissolved in water, they absorb water within 15 minutes and a gel diffusion layer is formed surrounding the dry bead, which is responsible for the modified iron release profile.

Ground, freeze dried beads are much less effective in-vivo. Also, in-vitro dissolution of ground, poorly formed dry gel beads rapidly results in a more immediate release profile.

EXAMPLE 10

In-Vitro Dissolution of Compositions

Known quantities of the beads containing approximately 2-4 mg of elemental iron were dissolved into 10 mL of buffered solution to ensure sink conditions with respect to the ferrous sulfate iron at pH 1.6 and maintained at 37° C. in a temperature controlled bath. The solutions were covered to prevent evaporation. At baseline and 15, 30, 45, 60, 90, 120 minute time points, 2×100 µL aliquots of the solution were removed for analysis of iron. One of the aliquots was immediately diluted into 900 µl water to measure the iron II content in the solution by the standard complexometric titration with 1,10 phenanthroline. The other aliquot was preserved for iron III measurement, where 100 µl of the solution was diluted to 900 µl 10 M HCl and left overnight at room temperature to oxide fully. Iron III content was determined using the standard laboratory isothiocyanate method. Experiments were conducted in triplicate.

EXAMPLE 11

Clinical Evaluation of Dry, Amorphous Iron-Protein Beads

Inclusion Criteria

Participants were considered eligible for enrollment into the study, if they were:
1. able to give written informed consent;
2. between 18 and 52 years of age;
3. non-pregnant, if female; and
4. in generally good health.

Exclusion Criteria

Subjects were excluded from the study if they met any of the following criteria:
1. were less than 18 and greater than 65 years of age;
2. were pregnant, lactating or wished to become pregnant during the study;
3. were menstruating within 3 days of the study visit;
4. were hypersensitive to any of the components of the test product;
5. suffered from a metabolic disorder;
6. had any evidence of current infection (viral, bacterial, other) as indicated by a raised white cell count;
7. were taking any iron supplements or preparations;
8. had a significant acute or chronic coexisting illness (cardiovascular, gastrointestinal, endocrinological, immunological, metabolic or any condition which contraindicated, in the investigators judgement, entry to the study);
9. had a condition or was taking a medication that the investigator believed would interfere with the objectives of the study, pose a safety risk or confound the interpretation of the study results;
10. consumed more than the recommended alcohol guidelines i.e. >21 alcohol units/week for males and >14 units/week for females;
11. had a history of illicit drug use;
12. were, in the opinion of the investigator, considered to be poor attendees or unlikely for any reason to be able to comply with the trial;

13. subjects were not to be receiving treatment involving experimental drugs. If the subject had been in a recent experimental trial, these must have been completed not less than 30 days prior to this study;
14. had a malignant disease or any concomitant end-stage organ disease.

Study Visits

The visit windows were set as outlined in the Table 1 and the text below.

TABLE 1

| Day | Screening Visit | Study Visit |
|---|---|---|
| Informed Consent | X | |
| Inclusion/Exclusion | X | |
| Vitals | X | |
| Demographic Data | X | |
| Fasting Blood Sample (8 ml) | X | |
| Urine Pregnancy Test (if applicable) | X | |
| Randomization | X | |
| Study Product Administered | | X |
| Fasting Blood Sampling (20 mls) | | X |
| Taste questionnaire | | X |
| Adverse Events recorded | | X |
| Concomitant Medications Record | | X |

Screening Visit (Visit 1)

Subjects were recruited from a volunteer database. An initial phone screen was performed, where subjects were asked questions regarding their eligibility and general health. At the baseline visit fasting venous blood sample (8 ml) was collected and a full blood count was performed, along with serum iron and ferritin. Eight females were selected to continue in the study, based on their serum iron and ferritin levels and subjects were requested to return to the study site within the next two weeks for the study visit. During this period they were instructed to follow their standard diet and exercise routine and not consume medications that could interfere with the assessment of the study product.

Study Visits

Subjects attended this visit fasting from food and tea/coffee since 10 pm the previous night. The study was to investigate the effects of oral supplementation of iron with the dry, amorphous iron-protein beads in comparison with wet gel-iron-protein beads where the iron is dissolved in water and also a commercially available iron supplement, comprising ferrous sulfate in acidified water, Spatone®. In the successive studies, subjects were randomly allocated into one of the two treatment groups and were given a single dose of a supplement, mixed with 100 mls of apple juice. A blood sample was collected immediately before drinking the supplement and at 2 hours and 4 hours after dosing. A total of 24 mls of blood was collected throughout the day. Water was consumed ad libitum, and after the 4-hour blood collection, a light snack was given to the subjects. Subjects were asked to complete a questionnaire relating to the taste, tolerability and palatability of the supplement. Subjects were queried about any changes in their health status. Any adverse events or serious adverse events were recorded. Subjects returned to the study site after a wash-out period of at least two weeks. During this period they were instructed to follow their standard diet and exercise routine and not consume medications that could interfere with the assessment of the study product. Subjects returned to the study site after a minimum wash-out of two weeks, and following an 10 hour overnight fast from food and tea/coffee. Subjects were crossed-over to the second phase of the study and were given a single dose of the alternative supplement at the same dosage as the supplement delivered in the first phase of the study, mixed with 100 mls of apple juice. Study visit procedures were as described above.

Removal of Subjects from the Study and Concomitant Medication

Subjects were withdrawn from the study if the subject elected independently to withdraw from the study; if he/she developed any condition, which contravened the original criteria; or was considered at any point to be unsuitable to continue the study, at the discretion of the investigator. No withdrawals occurred. Subjects were questioned about their medication history. The details of any medication taken were recorded in the participant case notes and case report form.

Biological Sample Collection and Analysis

A fasting blood sample (8 mls) was collected at the screening visit, and a full blood count (FBC), Serum iron and ferritin was assessed. During the intervention days, blood was also collected at baseline (8 mls), 2 hours (4 mls) and 4 hours (4 mls). Full Blood Count, serum iron, ferritin and iron binding capacity was measured at baseline, serum iron was assessed at 2, and 4 hours and ferritin and iron binding capacity was also measured. All samples were shipped to an approved contract laboratory for analysis. A total of 24 mls of blood was collected throughout the study.

Treatments Administered

We compared a wet gel iron-protein bead composition with ST1406 microbeads of the invention comprising iron predominantly in the ferrous (Fe2+) state. Also, we analysed the comparative performance of the ST1406 microbeads of the invention versus a solution of ferrous sulfate in acidified water.

Storage of Study Product

Study product was stored in a secure area with restricted access and was dispensed only to study subjects who had provided written consent. The investigative product was stored at room temperature away from moisture, direct heat and sunlight. Treatment doses were adjusted for any product remaining in the administration vehicle and, a priori, subjects were deemed ineligible if the dose administered was less than 30% of the prepared dose. None of the subjects were excluded on this basis. The in-vivo results are presented as area under the curve over the study period calculated using the trapezoidal method and adjusted for the final dose administered.

Statistical Analysis

For continuous variables, summary statistics were presented as the mean (SD) or median and 25th to 75th percentiles (interquartile ranges). Comparisons between groups were made using paired and independent-t, Mann-Whitney, or Chi-square tests where appropriate.

Results

Powder X-Ray analysis was performed using a Miniflex II Rigaku diffractometer with Ni-filtered Cu Kα radiation ($\lambda$=1.54 Å). The tube voltage and tube current used were 30 kV and 15 mA respectively. Each sample was scanned over 2 theta range 5-80° with a step size of 0.05°/s. As can be seen from FIGS. 16-19, the XRD traces for the physical combination of whey protein and FeSO4.7H2O in proportions similar to the composition of ST1406 (dry Fe2+ releasing beads) show the presence of peaks at scattering angles 2 theta (degrees)=12.9, 16.3, 19.9, 22.5, 26.3 and 30.1 which are absent from ST1406, confirming that the ferrous sulfate composition is largely in an amorphous physical state.

Figure 15:
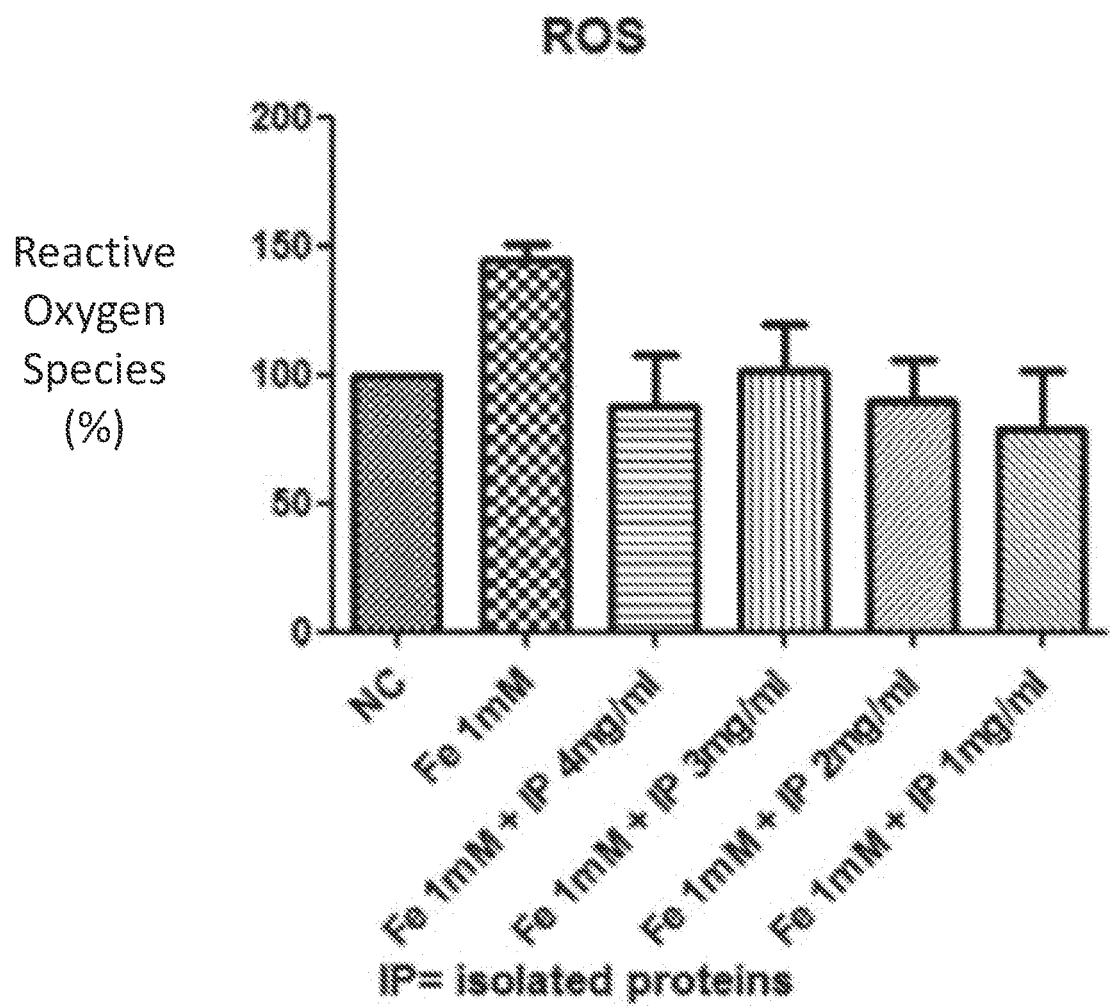
FIG. 15 depicts results demonstrating that low concentrations of isolated whey protein are able to normalise reactive oxygen species (ROS) generation in an adherent monolayer of the colorectal epithelial adenocarcinoma cell line CACO2 in response to iron. The vertical axis denotes ROS with the normal control (NC) set at 100%. IP refers to calcium depleted whey protein.

In some embodiments, isolated whey proteins combined with ferrous iron at low concentrations can increase CACO2 cell formation of reactive oxygen species (ROS). Even low concentrations of isolated whey proteins are able to normalise the ROS increase in CACO2 (see FIG. 15) caused by iron treatment highlighting the anti-oxidant potential of certain embodiments of the composition, which can be of benefit if the formulation contains ferrous iron.

In-Vivo Performance of ST1406 (Dried, Amorphous Iron-Protein Bead with Iron in Predominantly Fe2+ State) a Wet Gel Iron-Protein Bead Composition and a Solution of Ferrous Sulfate in Acidified Water.

Figure 7:
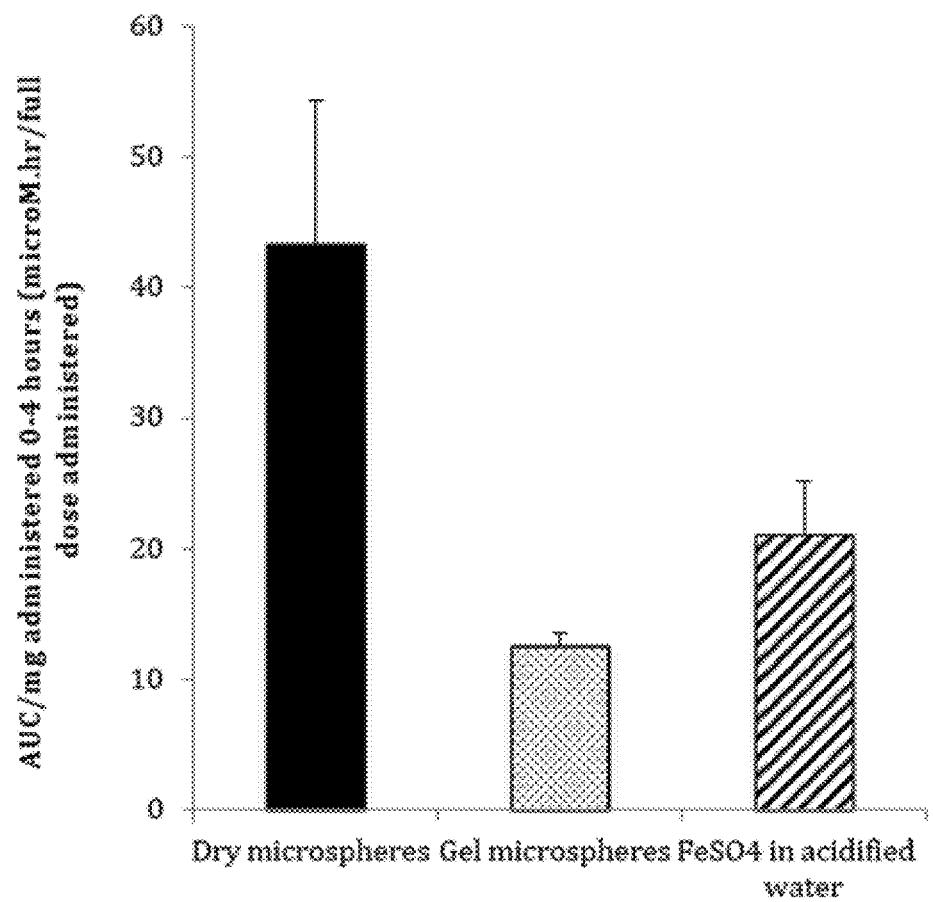
FIG. 7 depicts results demonstrating that an intermediate hydrogel (wet) formulation is less effective than dry ST1406 microbeads of the invention in vivo (p<0.05) using AUC measurements over 0-4 hours. Additionally, the hydrogels are more prone to oxidation and microbiological growth.

As shown in FIG. 7, the in vivo performance of ST1406 was superior to the wet-gel formulation ST1404 which was made in the same manner as ST1406, but stored in a sealed container before drying. During this process, the iron largely oxidized over a period of hours and the release of fe2+ was reduced in comparison with ST1406 dried amorphous microbeads of the invention. Iron absorption from the dried, amorphous iron-protein formulation (ST1406 with iron predominantly in the Fe2+ state), but not the wet gel iron-protein bead formulation, were superior to the market leading ferrous sulfate solution.

Figure 8:
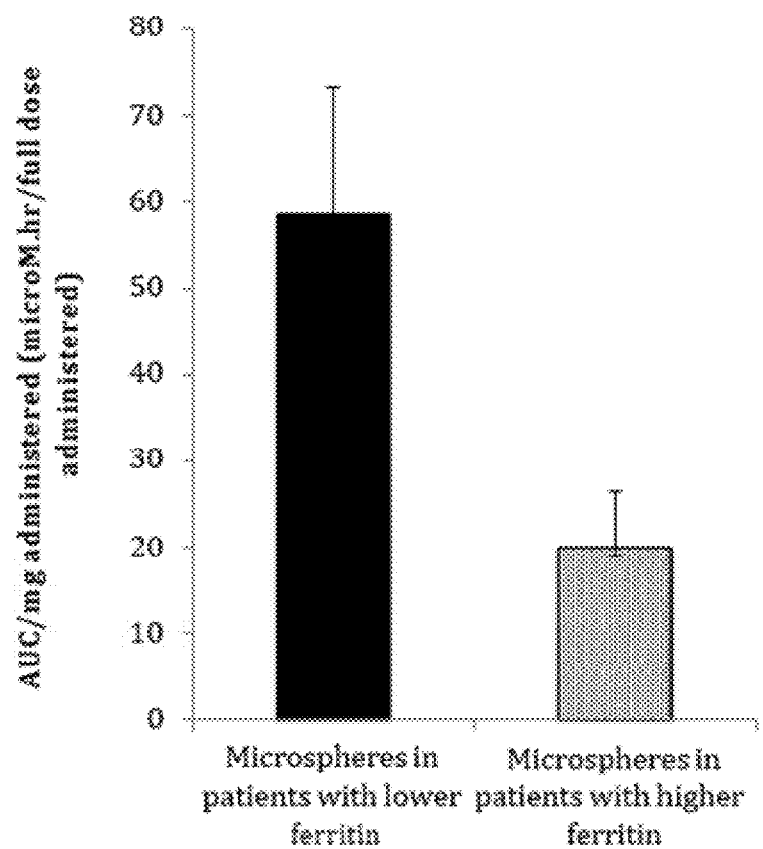
FIG. 8 depicts relative bioavailability measurements of ST1406 microbeads of the invention in subjects with lower ferritin and higher ferritin (p<0.05 for difference) using AUC measurements over 0-4 hours. These data are consistent with the view that the iron in microbeads of the invention are actively absorbed and that as ferritin levels decrease and DMT-1 expression increases, there is greater bioavailability of iron in the formulation.
Figure 9:
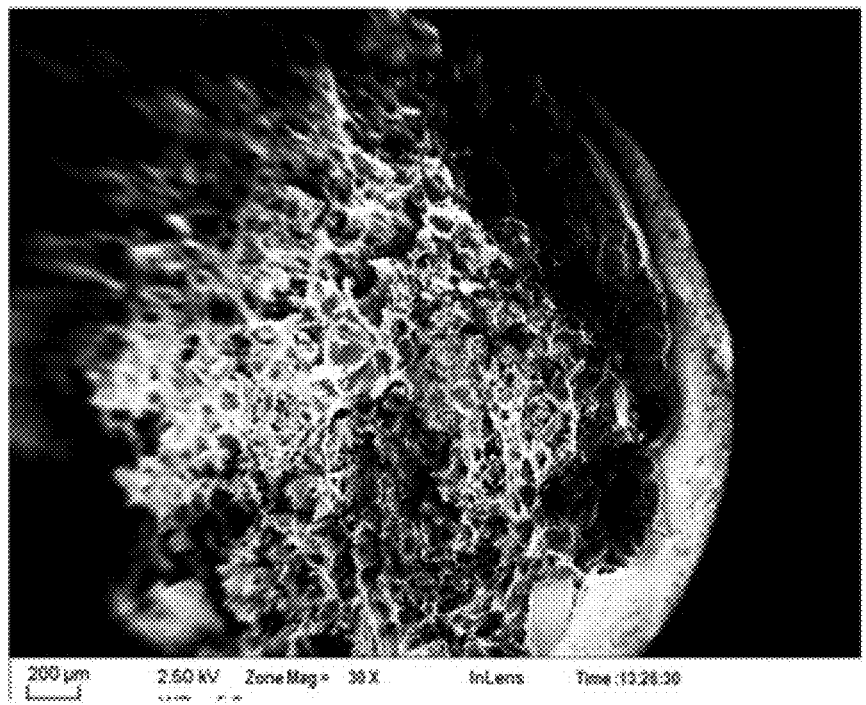
FIG. 9 is an SEM showing an image of a large bead at the intermediate hydrogel (wet) stage prepared for analysis by freeze drying to keep the surface features intact. The hydrogel interior network and morphologically distinct shell are evident at this stage.
Figure 10:
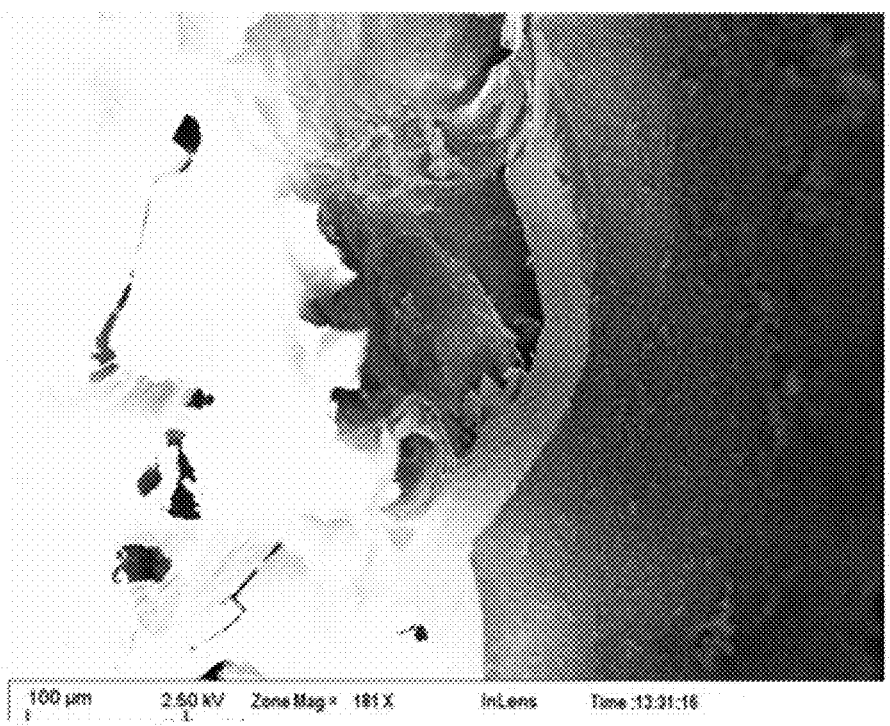
FIG. 10 is an SEM showing an image of the bead at the intermediate hydrogel (wet) stage prepared for analysis by freeze drying to keep the surface features intact with a close up of the skin formed on the microbead surface.

Finally, the performance of the dried, amorphous ST1406 iron-protein microbeads of the invention was compared in subjects with higher and lower iron stores measured by serum ferritin levels and the results are depicted in FIG. 8. This may suggest that the iron absorbed from the amorphous iron dried protein bead is absorbed via the DMT1 because its activity is inversely related to ferritin stores.

EXAMPLE 12

Stability Testing

It is important to note that intermediate gel beads are not stable with respect to oxidation and this is reflected in reduced release of ferrous iron (II) in dissolution media. In accordance with this, gel beads prepared for more than 24 hours have variable and poor performance clinically and are not scalable or commercially acceptable. Furthermore, these gel intermediates are prone to microbiological growth. ST1406 microbeads of the invention were found to be stable in that the dissolution profile at pH 1.6 and pH 6.6 was substantially unchanged with respect to iron II release for at least 6 months when stored in a sealed container at ambient conditions. For example, in one embodiment of the invention, when blister packed in a [1] hydroxyl propyl methyl cellulose (HPMC) capsule under ambient conditions and in a [2] HPMC capsule under Nitrogen in a sealed chamber at room temperature, the composition released 97.8%±3.5% and 100.4%±2.9% of the iron II content released at baseline (set at 100%) over 1 hour during dissolution experiments at pH 6.6 following long term storage. Furthermore, both compositions were free of objectionable microorganisms, including a Total Viable Count with a Maximum Tolerable amount of $10^3$ cfu/1000 mg, Total Yeast and Moulds Maximum Tolerable $10^2$ cfu/1000 mg, and *E-Coli* Absent.

EXAMPLE 13

Preparation of ST1406 25 mg Iron Capsule for Testing Versus Tardyferon 80 mg

Following protein heat denaturation the solution of aggregates was rapidly cooled to room temperature using constant agitation and then kept for 14 hours at 4° C. constantly agitated. Using the DTNB Thiol testing according to Ellmann's reaction (Ellman G L (1959). "Tissue sulfhydryl groups". *Arch. Biochem. Biophys.* 82 (1): 70-7. doi:10.1016/0003-9861(59)90090-6) the protein was sufficiently denatured following 45 minutes heating at 80° C. The resulting whey protein oligomer solution was extruded through a multinozzle plate into a curing solution maintained at 65° C., (4M at pH 3.2), containing ferrous sulfate 0.5M. Spherical microbeads were as described above in Example 1 and were washed with equal volumes of sterile, ultrapure water before drying in a fluidized bed dryer under nitrogen at 80° C. inlet temperature. The resulting dry microbeads had an iron concentration of 4.5% and were hand filled into HPMC capsuled to give a final dose of 25 mg elemental iron.

Figure 17:
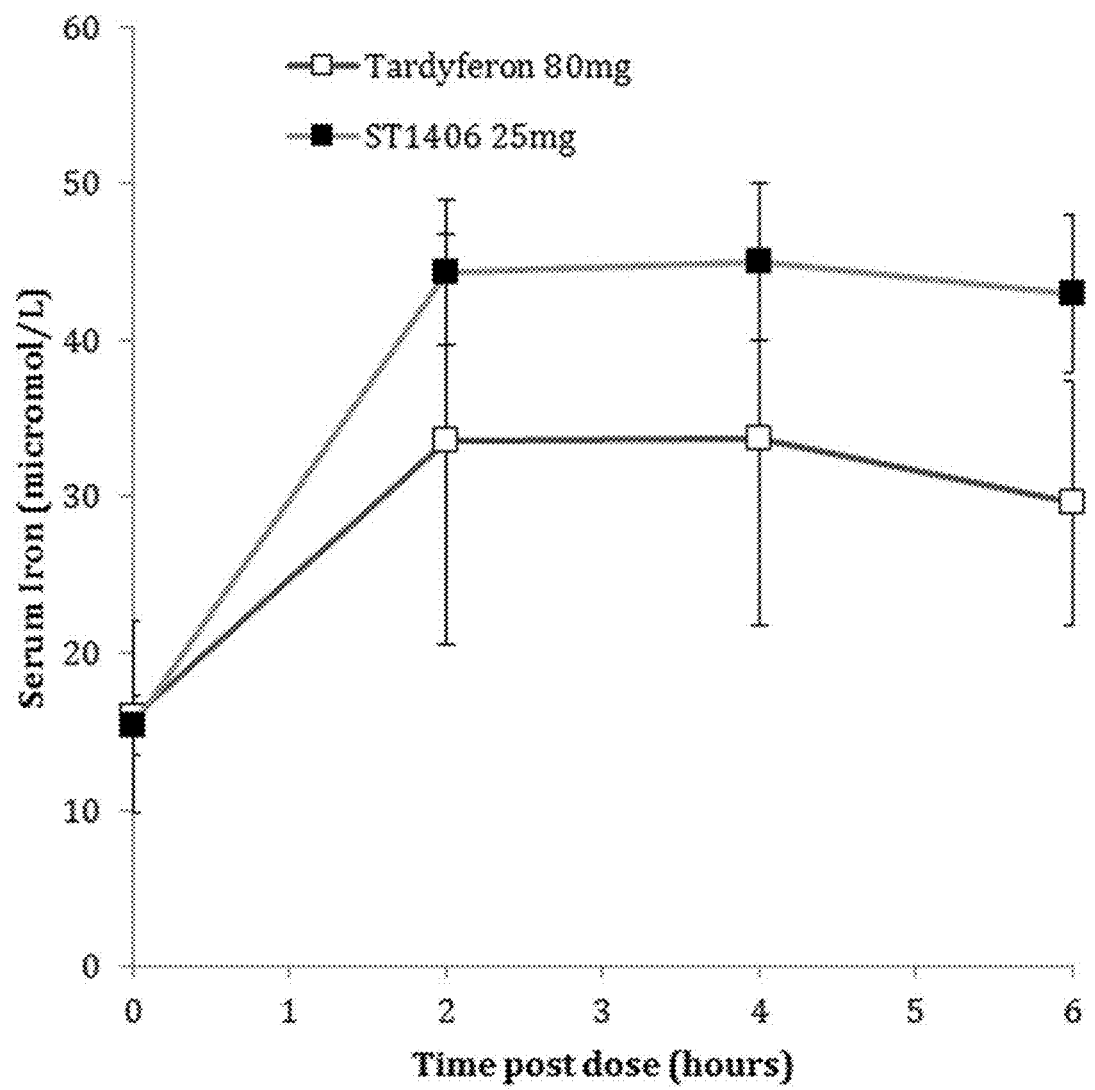
FIG. 17 shows the serum iron concentrations in fasting subjects (n=3) taking Tardyferon at an elemental iron dose of 80 mg and subsequently crossed over to ST1406 microbeads of the invention at an elemental iron dose of 25 mg

FIG. 17 shows the serum iron concentration of Tardyferon 80 mg and ST1406 25 mg following ingestion in fasting subjects (n=3) and cross-over to the alternative formulation. Tardyferon 80 mg is the trade name for a prolonged-release coated tablet containing ferrous sulfate. ST1406 25 mg was prepared according to Example 13. FIG. 17 shows that 25 mg ST1406 Iron caused a higher serum iron concentration than a 3× dose Tardyferon, a marketed ferrous sulfate formulation claiming gastroprotection, good tolerability and equivalent efficacy to immediate release formulations of ferrous sulfate.

EXAMPLE 14

Preparation of 1.3% Iron Microspheres

Figure 3:
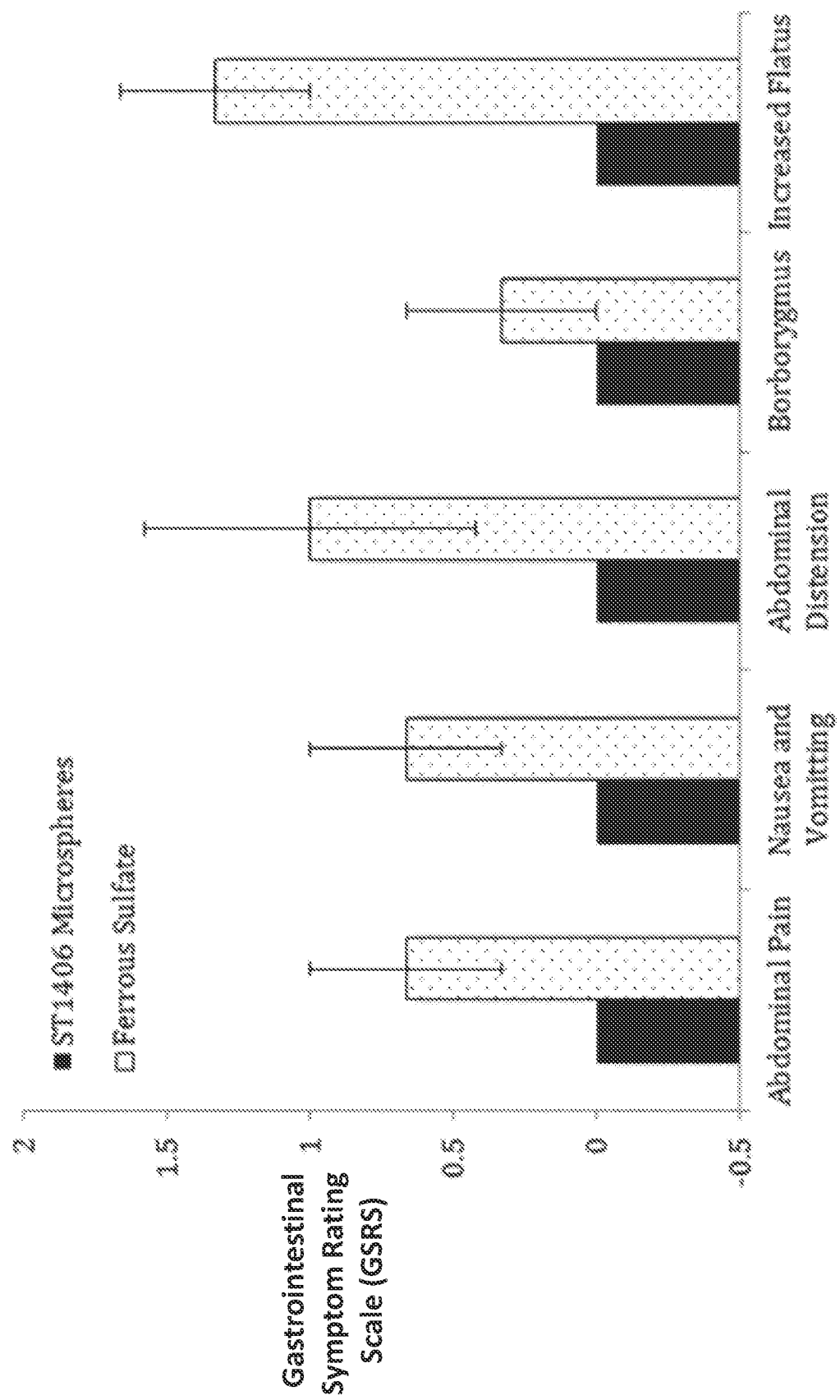
FIG. 3 depicts an example of the comparative gastrointestinal tolerability data for the ST1406 embodiment of the invention. Three subjects from the taste test had a history of intolerance to ferrous iron preparations, even at low doses, and suffered upper gastrointesinal symptoms during the taste test. In a separate study beads prepared in accordance with the invention or FeSO4.7H$_2$O in identical size 0 gelatin capsules were taken in the morning after fasting for 10 hours with baseline and 2 hour fasting blood draws. After 2 hours, a modified Gastrointestinal Symptom Rating Scale (GSRS) was showed show that beads prepared in accordance with the invention are well tolerated. Significantly higher symptoms scores were observed for abdominal pain/cramps, nausea, flatulance (all p=0.02) and constipation (p=0.03).
Figure 4:
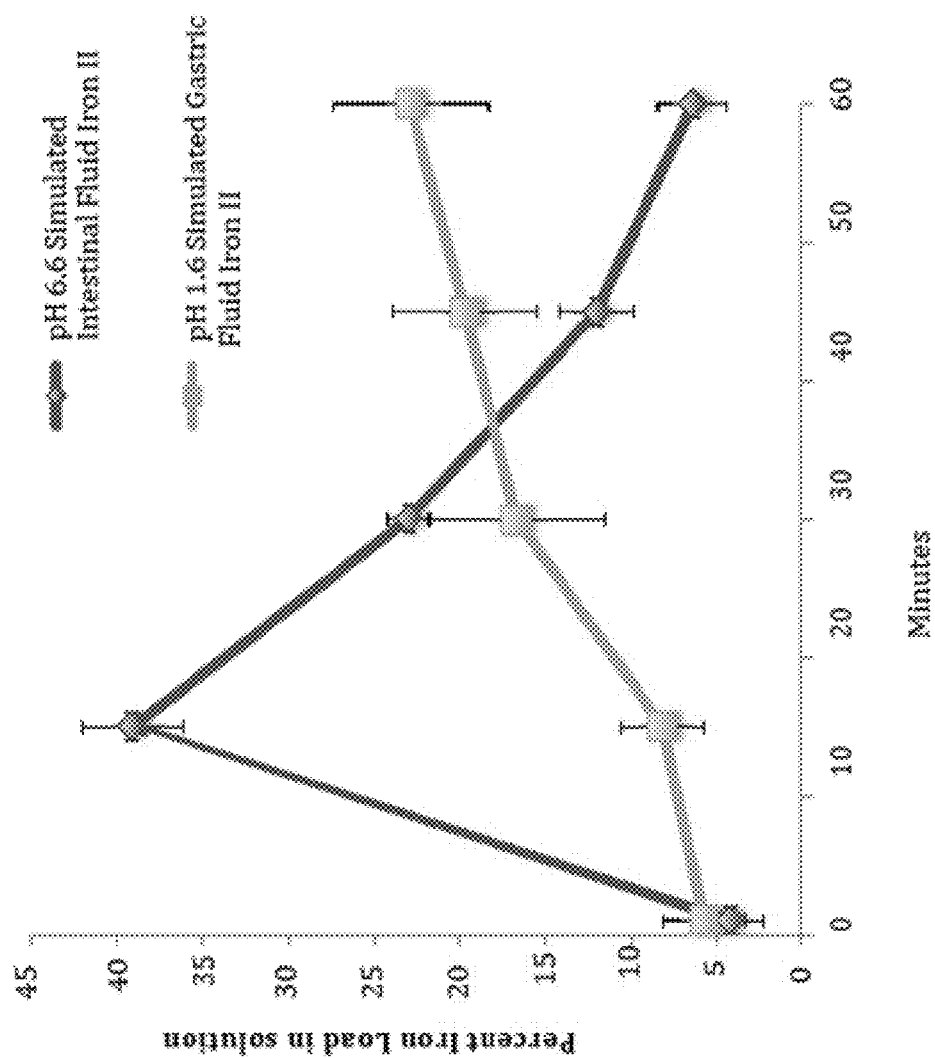
FIG. 4 depicts an example of the comparative iron II profile in dissolution from ST1406 microbeads of the composition at pH 1.6 and pH 6.6 in the presence of pepsin (pH 1.6 solution) and pancreatin (pH 6.6 solution). The detailed methodology is described below. This profile shows that the composition preferentially releases iron II in experimental conditions that mimic the small intestine—higher pH, digestive enzymes and bile salts.
Figure 5:
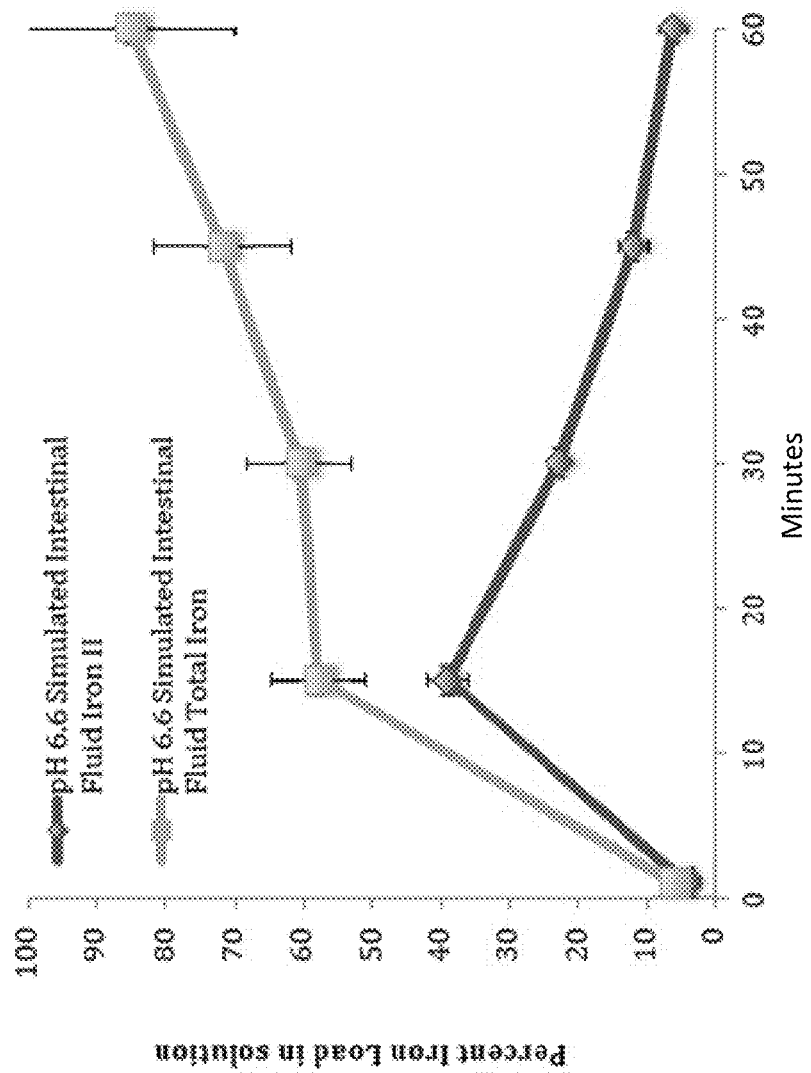
FIG. 5 depicts an example of the iron II and total iron (ferrous and ferric) profile in dissolution from the composition at pH 6.6 over 1 hour using the dissolution methodology described below in the presence of pancreatin and bile acids (pH 6.6 solution). Unlike ferrous sulfate, which undergoes oxidation and precipitates as ferric hydroxides, ST1406 microbeads of the invention maintain release of iron into solution.

Microspheres were made according to Example 1. After production the product was separated from the curing solution using a sieve and was washed with three volumes (equal to the volume of the beads after removal of curing solution) of ultrapure sterile water to yield microspheres containing about 1.3% iron after drying. Through observation, the microspheres were mono-dispersed, spherical and of equal size and shape and appeared to possess a skin on the outer surface. The bioavailability was much higher than comparable solutions of powdered ferrous sulfate and the microspheres demonstrated good palatability and tolerability, as shown in FIGS. 2 and 3.

EXAMPLE 15

Preparation of 2.5% or 4% Iron Microspheres

Microspheres were made according to Example 1. However the product was washed with two equal volumes of ultrapure sterile water to yield microspheres containing about 2.5% or about 4% iron after drying. 300 mg microspheres are put into a size zero capsule to give a 7-9 mg dose. These microspheres were administered to patients and provided superior clinical efficacy to equimolar ferrous sulfate and also to wet gel beads of the formulation (FIG. 7).

EXAMPLE 16

Preparation of 5% or 6% Iron Microspheres

Microspheres were made according to Example 1. However the product was washed with one equal volume of ultrapure sterile water. The microspheres were formulated into a 25 mg elemental iron equivalent in a HPMC capsule and had, for example a relative bioavailability superior to that of Tardyferon, a marketed formulation of ferrous sulfate with 80 mg elemental iron equivalents. (FIG. 17).

EXAMPLE 17

Preparation of 2.5% or 4% Iron Microspheres using L-Ascorbic Acid

Microspheres were made according to Example 1. However the product was cured in the curing solution additionally containing 100 mM L-ascorbic acid to reduce oxidation of the iron II. After production the product was separated from the curing solution using a sieve and was washed with two equal volumes of ultrapure sterile water to yield microspheres containing about 2.5% or 4% iron after drying.

EXAMPLE 18

Preparation of Zinc Sulfate Microspheres

Microspheres were made according to Example 1, however zinc heptahydrate sulfate was substituted for iron sulfate heptahydrate in the curing solution and had a resultant pH of 3.8. The produced microspheres were cured for 30 minutes in the curing solution. The product was separated from the curing solution using a sieve and was washed with two volumes of ultrapure sterile water to yield microspheres which were mono-dispersed, spherical and of equal size and shape. The microspheres demonstrated good palatability and tolerability. The resulting microspheres had a bland taste, making them highly palatable. In contrast, an acidified solution of zinc sulfate had poor palatability.

What is claimed is:

1. A composition comprising:
   iron; and
   a carrier comprising denatured protein, wherein the denatured protein comprises: denatured whey protein, denatured whey protein isolate, denatured beta lactoglobulin, or combinations thereof, and wherein the denatured protein is at least partially subjected to divalent metal ion removal; and
   acetate and acetic acid,
   wherein the composition releases less than 50 wt % of the total iron content as ferrous iron over the course of one hour in simulated gastric fluid at pH 1.6 and
   wherein the composition, when administered orally to a human, has a relative bioavailability of at least 120% that of an equimolar dose of an orally administered solution of ferrous sulfate in acidified water,
   wherein the total iron content is 1% to 2.5% as dry weight % of the composition,
   wherein the composition is in the form of microbeads, and
   wherein the moisture content of the composition is less than 10% by weight.

2. The composition of claim 1, wherein the composition is largely amorphous.

3. The composition of claim 1, wherein the denatured protein is at least 50%, 80% or 90% denatured.

4. The composition of claim 1, wherein the denatured protein contains at least 50%, 80% or 90% denatured beta lactoglobulin.

5. The composition of claim 1, said carrier comprising a core and a skin, said skin comprising a denatured aggregated protein, and wherein the composition is in the form of microbeads with a mean diameter of 2000 microns or less.

6. The composition of claim 1, wherein the denatured protein contains, excluding iron, less than 1% divalent metal ions (w/v).

7. The composition of claim 1, wherein the denatured protein contains less than 1% calcium (w/w).

8. The composition of claim 1, wherein the composition, when administered orally to a human, has a relative bioavailability of at least 150% that of an equimolar dose of an orally administered solution of ferrous sulfate in acidified water.

9. The composition of claim 1, wherein the composition releases less than 50 wt % of the total iron content as ferrous iron over the course of 30 minutes in simulated gastric fluid at pH 1.6.

10. The composition of claim 1, wherein the composition releases more than 80 wt % of the total iron content over the course of 2 hours in simulated intestinal fluid at pH 6.6.

11. The composition of claim 1, further comprising a stabilizer.

12. The composition of claim 11, wherein the stabilizer comprises ascorbic acid, ascorbate, or a combination thereof.

13. The composition of claim 12, wherein the iron:protein ratio is 1:20 to 1:5.

14. The composition of claim 1, wherein the iron in the composition comprises at least 50% ferrous iron.

15. The composition of claim 1, wherein the composition is stable with respect to ferrous iron content and microbiological burden, for at least 6 months when stored in a sealed container at ambient conditions.

16. An edible formulation comprising the composition of claim 1, wherein the edible formulation is a powder, prenatal vitamin formulation, multivitamin formulation, supplement, chewable supplement, gummy, food, beverage, animal feed, tablet, capsule, or suspension.

17. A composition comprising:
    iron;
    a carrier comprising: denatured whey protein, denatured whey protein isolate, denatured beta lactoglobulin, or combinations thereof, wherein the denatured protein is at least partially subjected to divalent metal ion removal; and
    acetate and acetic acid
    wherein the iron:protein ratio, by weight, is 1:100 to 1:10,
    wherein the denatured protein contains, excluding iron, less than 1% divalent metal ions (w/v),
    wherein the moisture content of the composition is less than 10% by weight,
    wherein the carrier comprises a denatured aggregated protein matrix core and a denatured aggregated protein skin,
    wherein at least 50 wt % of the iron is ferrous iron,
    wherein the composition releases less than 20% of the total iron content as ferrous iron over the course of 30 minutes in simulated gastric fluid at pH 1.6,
    wherein the composition, when administered orally to a human, has a relative bioavailability at least 150% that of an equimolar dose of an orally administered solution of ferrous sulfate in acidified water;
    wherein the composition is in the form of microbeads, and
    wherein the composition comprises 0.5% to 2.5% iron as a dry weight % of the composition.

18. A method of increasing the serum iron in a mammal in need thereof comprising administering a composition comprising:
    iron;
    a carrier comprising denatured protein, wherein the denatured protein comprises: denatured whey protein, denatured whey protein isolate, denatured beta lactoglobulin, or combinations thereof, and wherein the denatured protein is at least partially subjected to divalent metal ion removal; and acetate and acetic acid
wherein the iron:protein ratio, by weight, is 1:100 to 1:10,
wherein the composition releases less than 50% of the total iron content as ferrous iron over the course of one hour in simulated gastric fluid at pH 1.6,
wherein the composition, when administered orally to a human, has a relative bioavailability at least 120% that of an equimolar dose of an orally administered solution of ferrous sulfate in acidified water,
wherein the denatured protein contains, excluding iron, less than 1% divalent metal ions (w/v),
wherein the composition is in the form of microbeads; and
wherein the composition comprises 0.5% to 2.5% iron as a dry weight % of the composition.

19. A composition comprising:
iron;
a carrier comprising denatured protein, wherein the denatured protein comprises: denatured whey protein, denatured whey protein isolate, denatured beta lactoglobulin, or combinations thereof, and wherein the denatured protein is at least partially subjected to divalent metal ion removal; and
acetate and acetic acid
wherein the iron:protein ratio, by weight, is 1:100 to 1:10,
wherein the composition releases less than 70 wt % of the total iron content as ferrous iron over the course of one hour in simulated gastric fluid at pH 1.6,
wherein the composition, when administered orally, has a relative bioavailability at least 120% that of an equimolar dose of an orally administered solution of ferrous sulfate in acidified water and,
wherein the denatured protein contains, excluding iron, less than 1% divalent metal ions (w/v),
wherein the moisture content of the composition is less than 10% by weight,
wherein the composition is in the form of microbeads, and
wherein the composition comprises 0.5% to 2.5% iron as a dry weight % of the composition.

20. The composition of claim 19, further comprising a stabilizer.

21. The composition of claim 19, wherein the iron in the composition comprises at least 50% ferrous iron, and wherein the composition is in the form of microbeads with a mean diameter of 2000 microns or less.

* * * * *